United States Patent
Pandey et al.

(10) Patent No.: US 9,821,062 B2
(45) Date of Patent: Nov. 21, 2017

(54) CYANINE DYE COMPOUND AND PREPARATION METHOD THEREFOR, AND DUAL-FUNCTION AGENT FOR PHOTODYNAMIC THERAPY AND PREPARATION METHOD THEREFOR

(71) Applicant: ZHEJIANG HISUN PHARMACEUTICAL CO., LTD., Zhejiang (CN)

(72) Inventors: Ravindra K. Pandey, East Amherst, NY (US); Nayan Patel, Buffalo, NY (US); Manivannan Ethirajan, Cheektowaga, NY (US); Hua Bai, Zhejiang (CN); Zhenliang Chen, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 14/758,427

(22) PCT Filed: Feb. 6, 2013

(86) PCT No.: PCT/CN2013/071445
§ 371 (c)(1),
(2) Date: Jun. 29, 2015

(87) PCT Pub. No.: WO2014/101339
PCT Pub. Date: Jul. 3, 2014

(65) Prior Publication Data
US 2015/0329490 A1    Nov. 19, 2015

(30) Foreign Application Priority Data
Dec. 28, 2012 (CN) .......................... 2012 1 0598014

(51) Int. Cl.
| C07B 47/00 | (2006.01) |
| C07D 487/22 | (2006.01) |
| A61K 41/00 | (2006.01) |
| C09B 23/04 | (2006.01) |
| C07D 403/14 | (2006.01) |
| C07D 209/60 | (2006.01) |

(52) U.S. Cl.
CPC ...... *A61K 41/0057* (2013.01); *A61K 41/0071* (2013.01); *C07D 209/60* (2013.01); *C07D 403/14* (2013.01); *C07D 487/22* (2013.01); *C09B 23/04* (2013.01)

(58) Field of Classification Search
None
See application file for complete search history.

(56) References Cited

U.S. PATENT DOCUMENTS

| 2004/0141920 A1 | 7/2004 | Achilefu et al. |
| 2004/0241095 A1 | 12/2004 | Achilefu et al. |
| 2009/0124792 A1 | 5/2009 | Achilefu et al. |

FOREIGN PATENT DOCUMENTS

| CN | 102268191 A | 12/2011 |
| JP | 07287346 | * 10/1995 |
| WO | 03/065888 A1 | 8/2003 |
| WO | 2006/019775 A1 | 2/2006 |
| WO | 2009/012109 A2 | 1/2009 |
| WO | 2012/006009 A1 | 1/2012 |

OTHER PUBLICATIONS

Chen, et. al.; Bioconjugate Chemistry (2005), 16(5), 1264-1274.*
International Search Report mailed Oct. 3, 2013; PCT/CN2013/071445.
Hyeran Lee, et al; "Heptamethine Cyanine Dyes with a Robust C-C Bond at the Central Position of the Chromophere", J. Org Chem, Sep. 29, 2006;71(20):7862-5.
Hyeran Lee, et al; "Synthesis and Spectral Properties of Near-Infrared Aminophenyl-, Hydroxyphenyk and Phenyl-Substituted Heptamethine Cyanines", J. Org. Chem, 73(2), pp. 7234-7725; Published on Web Dec. 21, 2007.
Michael P.A. Williams, et al; "Synthesis, Photophysical, Electrochemical, Tumor-Imaging, and Phototherapeutic Properties of Purpurinimide-N-substituted Cyanine Dyes joined with Variable Lengths of Linkers", Bioconjugate Chemistry; 22(11):2283-95; Epub Oct. 21, 2011.
Extended European Search Report dated May 20, 2016; Appln. No. 13868199.4-1452/2940021; PCT/CN2013071445.

* cited by examiner

*Primary Examiner* — Jeffrey H Murray
(74) *Attorney, Agent, or Firm* — Ladas & Parry LLP

(57) ABSTRACT

Disclosed are a cyanine dye compound and a preparation method therefor, and a dual-function agent for photodynamic therapy and a preparation method therefor. The provided cyanine dye compound is connected to multiple markers, which improves the accuracy of combination of dye and tumor cells, effectively reduces the background value, and avoids excessive residues in the liver. The provided cyanine dye compound is conjugated with the photosensitizer at 2'" position, so that tumor highly absorbs the conjugates.

9 Claims, 4 Drawing Sheets

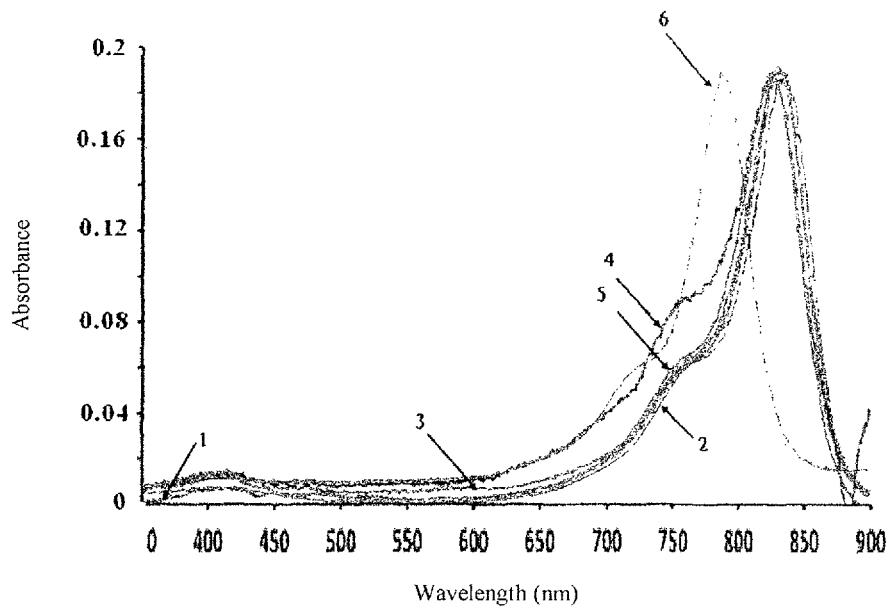
Figure 1
Figure 2(a)  Figure 2(b)  Figure 2(c)  Figure 2(d)  Figure 2(e)  Figure 2(f)  Figure 2(g)
Figure 2(h)  Figure 2(i)  Figure 2(j)  Figure 2(k)  Figure 2(l)  Figure 2(m)  Figure 2(n)
Figure 2(o)  Figure 2(p)  Figure 2(q)  Figure 2(r)  Figure 2(s)  Figure 2(t)  Figure 2(u)
Figure 2

Figure 8(a)     Figure 8(b)     Figure 8(c)     Figure 8(d)
Figure 8
Mice with pulmonary metastatic tumor     lung
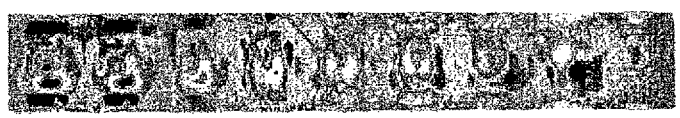
Depth    1mm   3mm   5mm   7mm   9mm   11mm   13mm   15mm   18mm
Control
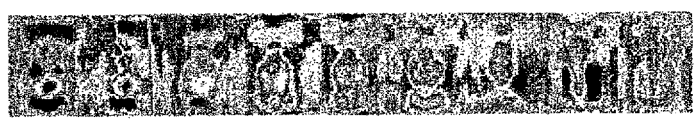
Liver
Figure 9

CYANINE DYE COMPOUND AND PREPARATION METHOD THEREFOR, AND DUAL-FUNCTION AGENT FOR PHOTODYNAMIC THERAPY AND PREPARATION METHOD THEREFOR

The present application claims the priority of Chinese Patent Application No. 201210598014.9, filed with the Chinese State Intellectual Property Office on Dec. 28, 2012, and entitled "CYANINE DYE COMPOUND, PREPARATION METHOD OF CYANINE DYE COMPOUND, DUAL-FUNCTIONAL AGENT FOR PHOTODYNAMIC THERAPY AND PREPARING METHOD OF DUAL-FUNCTIONAL AGENT", which is incorporated herein by reference in its entirety.

FIELD OF THE INVENTION

The present invention relates to the field of medicine, in particular to a cyanine compound and preparation method thereof, as well as a dual-function agent for photodynamic therapy and preparation method thereof.

BACKGROUND

According to the statistics of World Health Organization (WHO), 10 million people have suffered from malignant tumors around the world each year, among which about 6 million people have died from the malignant tumors, accounting for 12% of the global death toll. In China, there have been 1.8 million new patients with a malignant tumor each year, causing a death toll of 1.4 million with 1.3 patients dying from malignant tumors every 3 minutes; moreover, the incidence rate of the malignant tumors has shown a trend of sharp increase.

Imaging technology is one of tools indispensable to tumor research and clinic therapy thereof. Currently, there have been a variety of non-fluorescent in vivo imaging technologies such as computed tomography (CT), magnetic resonance imaging (MRI), positron emission tomography (PET), etc. The biggest problem with these methods is that the specificity and sensitivity are insufficient. Visible light imaging technologies have a high resolution for tumor detection and give signals which are capable of providing molecular information of a biological tissue and showing changes of important physiological parameters, among which a fluorescent imaging technology labels tumor cells with an imaging agent, thus imaging the tumor cells and achieving a better effect of resolution. A cyanine dye compound may be used as a tumor imaging agent, and the instrument applied for its imaging does not need invasion into an organism, which makes it possible to achieve tumor imaging with an ordinary LED screen.

However, most of cyanine dyes possess no selectivity to a specific organ and tissue, and thus have to be connected to bioactive carriers such as proteins, polypeptides, lipids, saccharides and other markers such that the dyes are possible to be combined with a target to enter a specific region. Therefore, the cyanine dyes which may be used as imaging agents currently have a general drawback of insufficient targeting, which tend to retain in the live and generally have a high background value in vivo.

In addition, due to the capability of producing reactive oxygen, the cyanine dye may also be used as a photosensitizer in photodynamic therapy (PDT) for tumor treatment. PDT is a novel therapy for selectively treating a disease such as tumor through a photodynamic reaction in combination with a photosensitizer. PDT is a therapeutic method with no systemic, organ or tissue toxicity, and is noninvasive, which may be reused as a main or an auxiliary means. However, cyanine dyes with different structures have different properties, and also have different roles in the PDT therapy. Currently, the commonly-used merocyanine-based cyanine dye is OXO or MC540, with the former having no strong stability and being prone to be used as a photosensitizer, while the latter having poor photosensitization and being more suitable for detection of tumor cells.

Therefore, the development of a dual-function agent which can have both functions of a photosensitizer and an imaging agent has become the research focus. Conjugates formed by the conjugation of a cyanine dye with a photosensitizer have a good photosensitivity and imaging effect, and are very suitable for use as a dual-function agent in photodynamic therapy. Such compounds includes a biochip made by binding of a cyanine dye Cy5 to an antibody, or a cyanine dye-peptide conjugate, etc. However, for these compounds, the antibody is used as a marker, which would influence the half-life of immunogen and plasma. More importantly, due to the specificity for the combination of a marker and a target molecule, use of such a conjugate is greatly limited.

In summary, a tumor imaging agent having good targeting and a low background value as well as a dual-function agent in photodynamic therapy still need to be developed.

SUMMARY OF THE INVENTION

In view of the above, the present invention provides a cyanine dye and preparation method thereof, as well as a dual-function agent for photodynamic therapy and preparation method thereof. The cyanine dye compound provided by the present invention has a good imaging effect as an imaging agent, and as a dual-function agent in photodynamic therapy, has a wider range of application and exhibits both of good therapeutic and imaging effects.

The present invention provides a compound having a structure as shown in formula I,

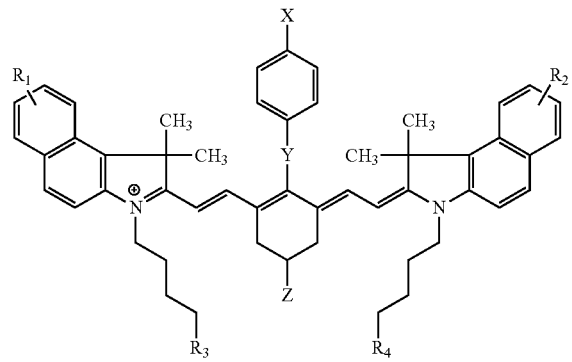

Formula I wherein $R_1$ and $R_2$ are independently selected from hydrogen, alkaryl, fluorinated groups, and sulfonated groups;

$R_3$ and $R_4$ are independently selected from —H, —$SO_3H$, —$SO_3Na$, —COOH, —OH, and —$NH_2$;

X is selected from —H, —COOH, —$NH_2$, —NH-$A_1$, —NH—CO-$A_2$, and —CO—NH-$A_3$;

Y is selected from —O—, —S—, —NH—, and —$CH_2$—; alternatively, Y is absent, being a single bond;

Z is selected from —H, —COOH, —COOEt, —NH$_2$, —NH-A$_1$, —NH—CO-A$_2$, and —CO—NH-A$_4$;

A$_1$, A$_2$, A$_3$ and A$_4$ are independently any substituent.

The compound having a structure as shown in formula I provided in the present invention is a cyanine dye compound.

In some embodiments of the present invention, the compound provided according to the present invention includes a compound having a structure as shown in formula II, Formula II

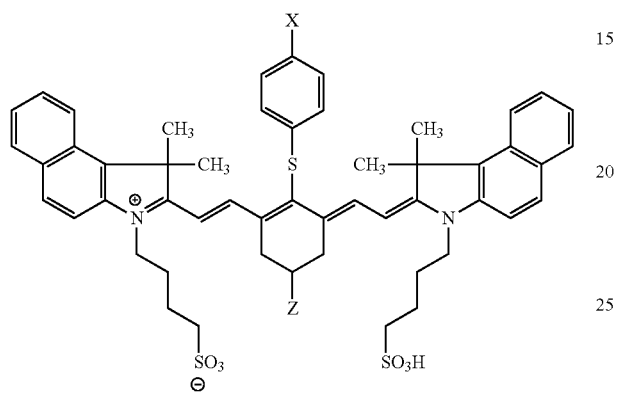

wherein X is any one of —H, —COOH, —NH$_2$, and —CO—NH-A$_3$;

Z is any one of —H, —COOH, —COOEt, —NH$_2$, and —CO—NH-A$_4$;

A$_3$ is peptide, saccharide or folic acid derivative;

A$_4$ is —C$_6$H$_5$, DOTA, DTPA, peptide, saccharide or folic acid derivative.

In other embodiments of the present invention, the compound provided according to the present invention has a structure as shown in any one of formula III to formula X:

Formula III

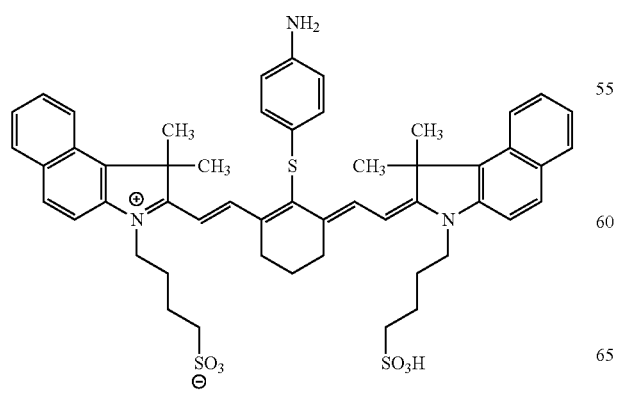

Formula IV

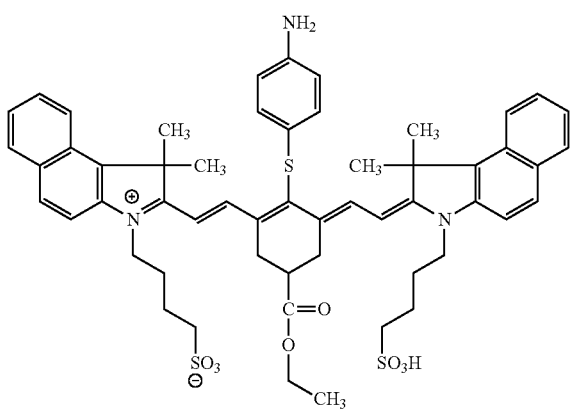

Formula V

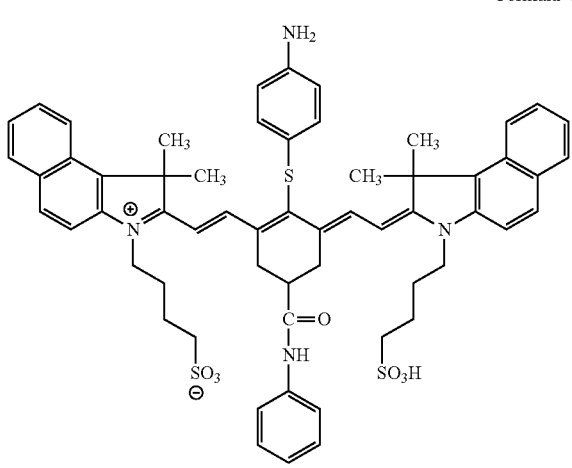

Formula VI

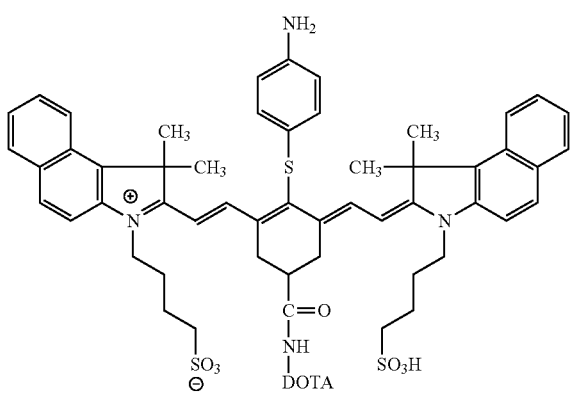

-continued

Formula VII

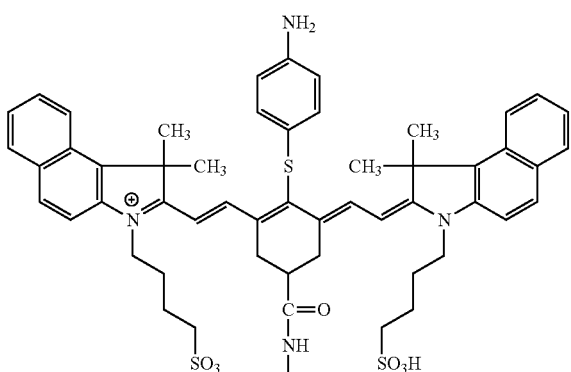

Formula VIII

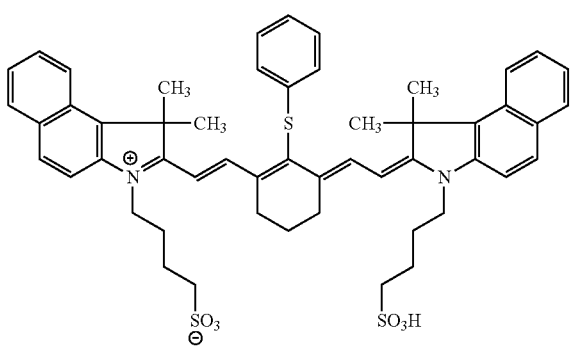

Formula IX

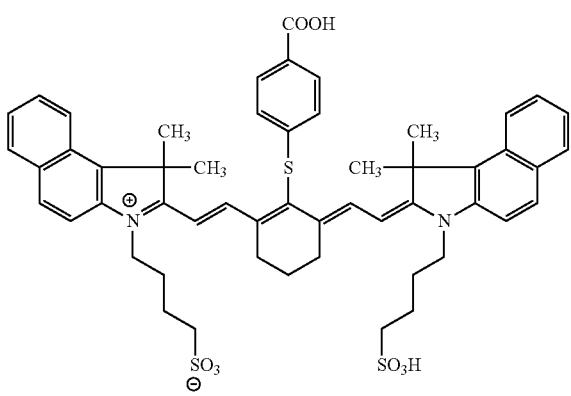

Formula X

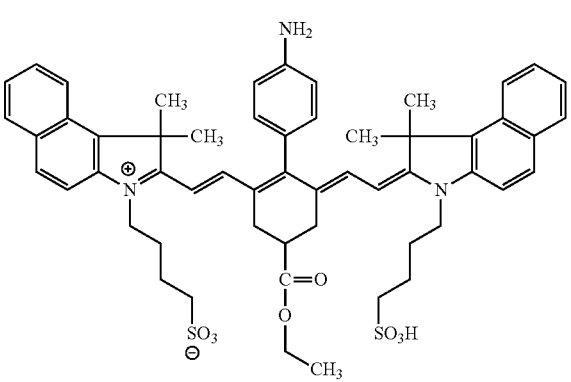

The cyanine dye compound provided according to the present invention is a novel cyanine dye, which may be specifically positioned in a tumor tissue, and has a more preferable positioning function to tumor relative to a normal tissue.

In some embodiments of the present invention, the compound provided according to the present invention includes a compound having a structure as shown in formula XI, Formula XI

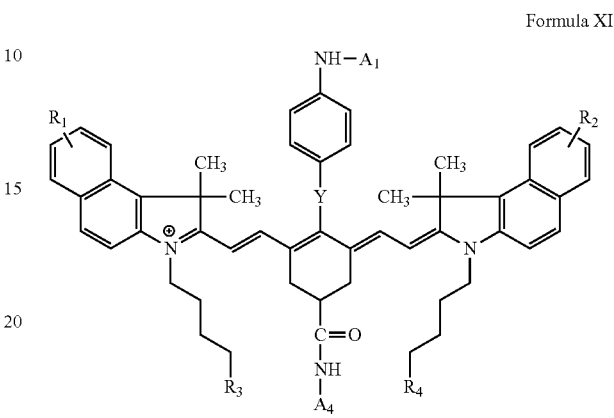

wherein Y is O, S, —NH—, or —CH$_2$—; alternatively, Y is absent, being a single bond;

R$_1$ and R$_2$ are independently selected from hydrogen, alkaryl, fluorinated groups or sulfonated groups;

R$_3$ and R$_4$ are independently selected from —H, —SO$_3$H, —SO$_3$Na, —COOH, —OH or —NH$_2$;

A$_1$ is -A$_5$-A$_6$, —H, maleimide, or a maleimide analogue substituted with F-18 or I-124, in which A$_5$ is carbonyl, alkyl or an aryl chain; and A$_6$ is maleimide, a maleimide analogue substituted with F-18 or I-124, peptide, saccharide, folic acid, tetrapyrrole ring or reduced tetrapyrrole ring;

A$_4$ is —(CH$_2$)$_n$-PS, in which n=0 to 6, and PS is glycosyl, tetrapyrrole ring or reduced tetrapyrrole ring, RGD peptide, iRGD peptide, DOTA, DTPA or triamino ester;

preferably, the tetrapyrrole ring includes, but is not limited to, chlorin, bacteriochlorin, purpurin imide and rhodopurpurin imide.

In other embodiments of the present invention, the compound provided according to the present invention has a structure as shown in formula XII, Formula XII

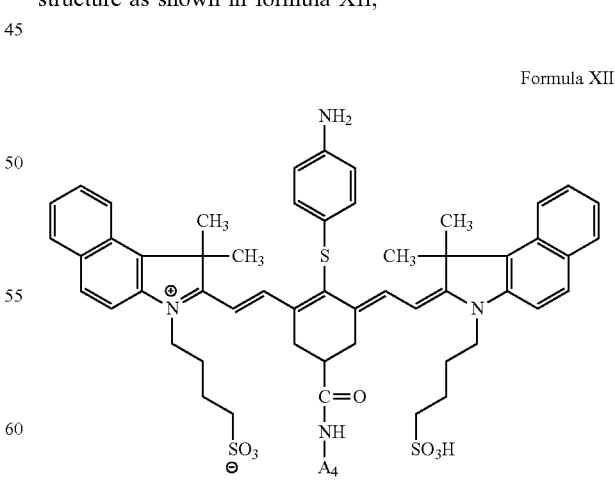

wherein A$_4$ is RGD peptide, iRGD peptide, glycosyl, DTPA, DOTA, triamino ester or —(CH$_2$)$_n$-PS in which n=0 to 6, and PS has a structure as shown in formula XIII, formula XIV or formula XV;

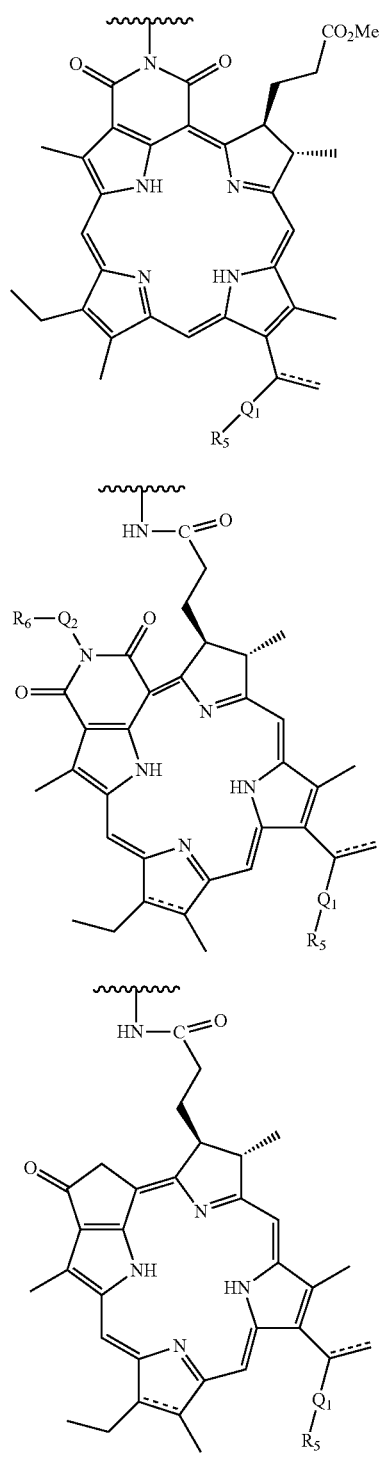

Formula XIII

Formula XIV

Formula XV

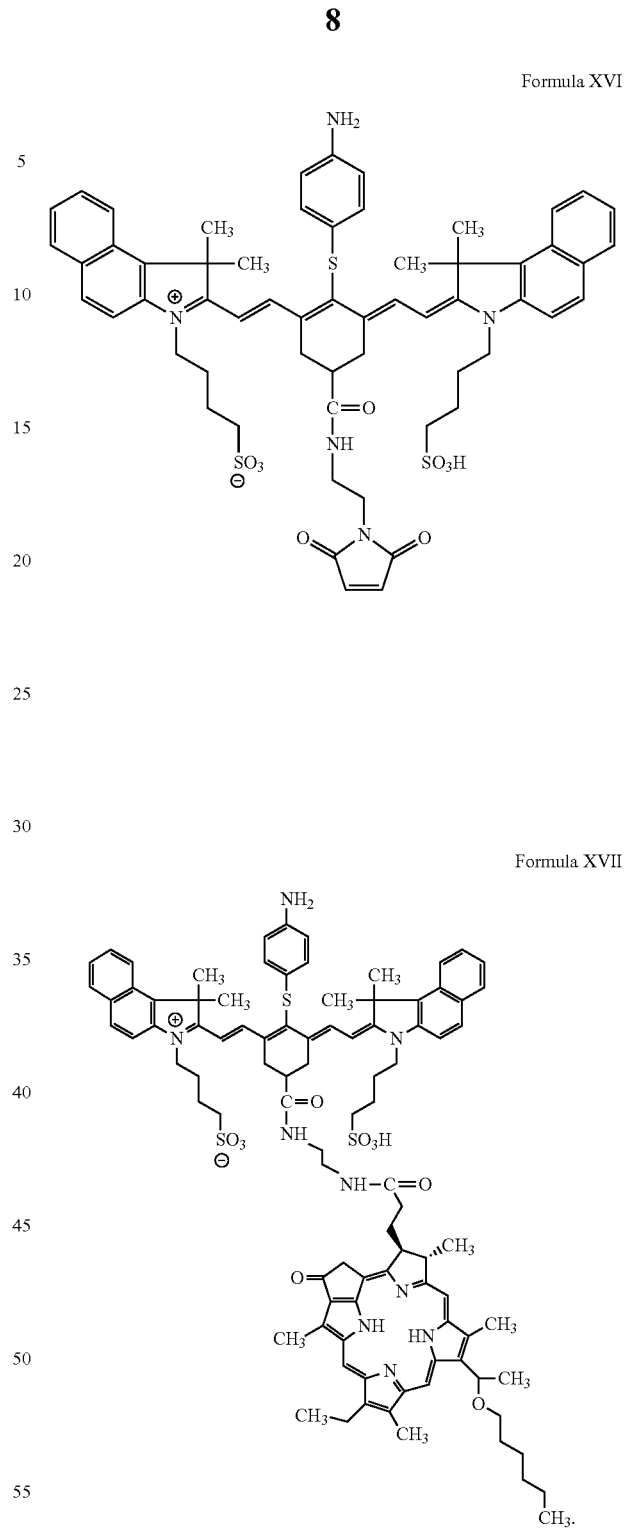

Formula XVI

Formula XVII wherein ≔ represents a single bond or a double bond; $Q_1$ and $Q_2$ are independently —O—, alkyl, aryl or reduced aryl; $R_5$ and $R_6$ are independently alkyl or alkyl labelled with F-18, iodobenzyl or iodobenzyl labelled with I-124.

In other embodiments of the present invention, the compound provided according to the present invention has a structure as shown in formula XVI or formula XVII, The compound provided according to the present invention allows the photosensitizer to be conjugated at 2''' position with the cyanine dye. Due to the presence of the conjugated system, the absorption effect of tumor thereto may be increased.

Furthermore, the present invention also provides an intermediate for synthesis of a compound having a structure as shown in formula I, which intermediate has a structure as shown in any one of formula XVIII to formula XXII, Formula I

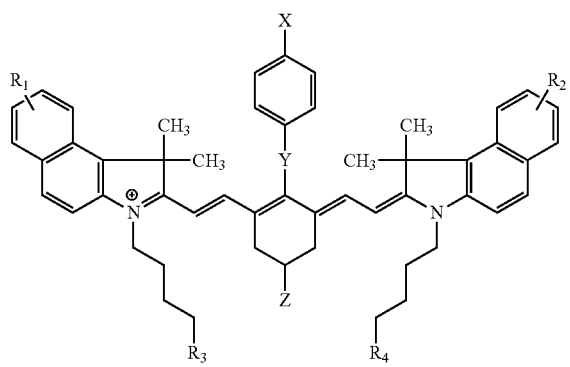

wherein $R_1$ and $R_2$ are independently selected from hydrogen, alkaryl, fluorinated groups, and sulfonated groups;

$R_3$ and $R_4$ are independently selected from —H, —$SO_3H$, —$SO_3Na$, —COOH, —OH, and —$NH_2$;

X is selected from —H, —COOH, —$NH_2$, —NH-$A_1$, —NH—CO-$A_2$, and —CO—NH-$A_3$;

Y is selected from —O—, —S—, —NH—, and —$CH_2$—; alternatively, Y is absent, being a single bond;

Z is selected from —H, —COOH, —COOEt, —NH-$A_1$, —NH—CO-$A_2$, and —CO—NH-$A_4$;

$A_1$, $A_2$, $A_3$ and $A_4$ are independently any substituent;

Formula XVIII

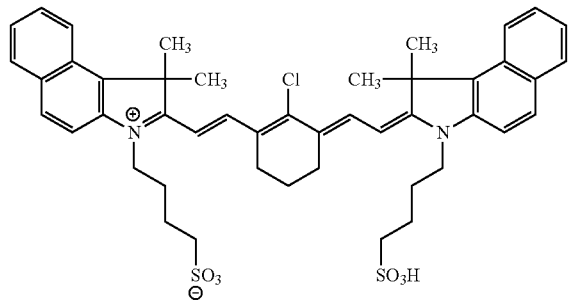

Formula XIX

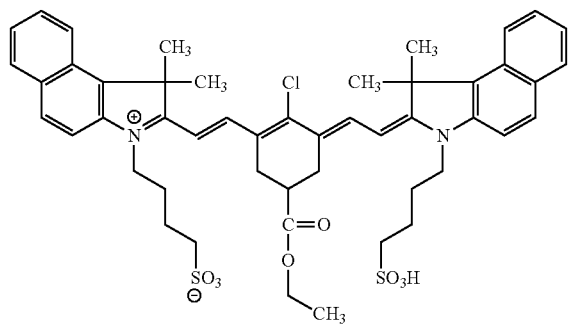

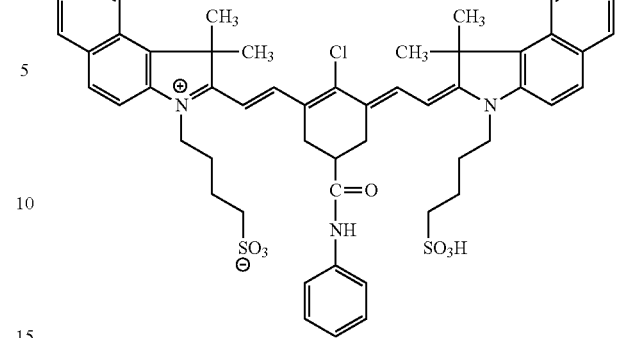

Formula XXI

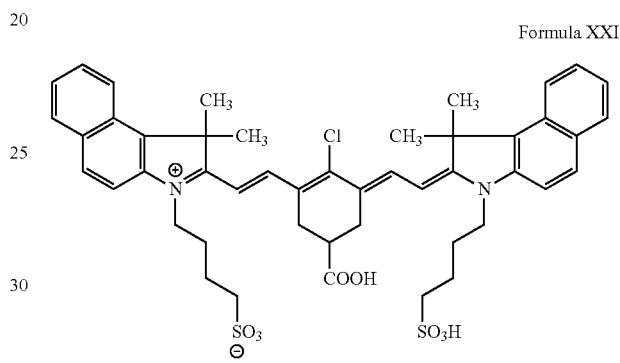

Formula XXII

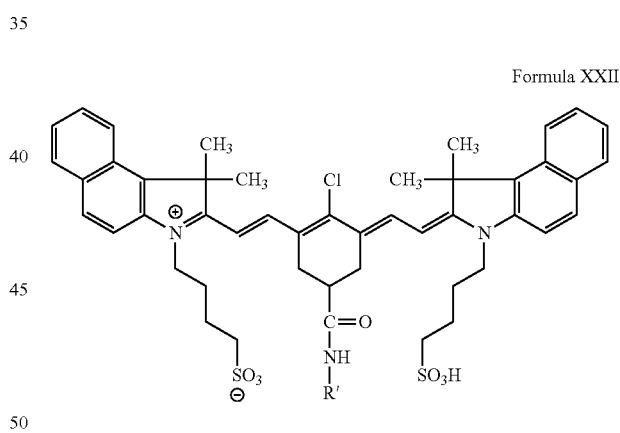

wherein R' is any one of maleimide, a maleimide analogue with or without I-124 and/or F-18, tetrapyrrole ring with or without I-124 and/or F-18, reduced tetrapyrrole ring, RGD peptide, iRGD peptide, glycosyl, DOTA, DTPA, and tri-amino ester;

preferably, the tetrapyrrole ring includes, but is not limited to, chlorin, bacteriochlorin, purpurin imide and rhodopurpurin imide.

The intermediate provided according to the present invention may also be used as a cyanine dye for preparation of a medicament for tumor treatment.

The present invention further provides use of a compound having a structure as shown in formula I in the preparation of a tumor imaging agent and/or in the preparation of a dual-function agent for tumor imaging and tumor treatment:

Formula I

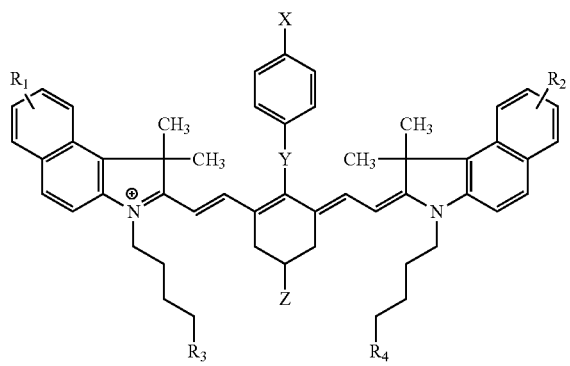

Formula IV

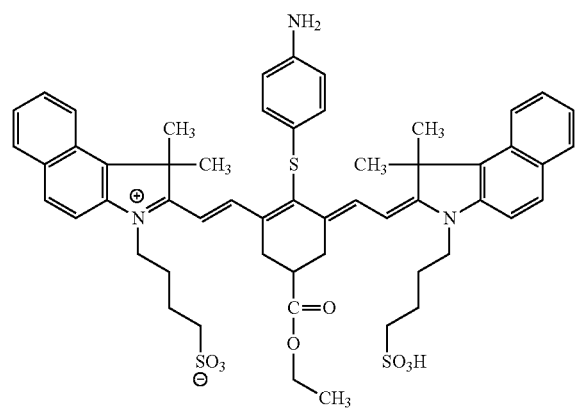

wherein $R_1$ and $R_2$ are independently selected from hydrogen, alkaryl, fluorinated groups, and sulfonated groups;

$R_3$ and $R_4$ are independently selected from —H, —$SO_3H$, —$SO_3Na$, —COOH, —OH, and —$NH_2$;

X is selected from —H, —COOH, —$NH_2$, —NH-$A_1$, —NH—CO-$A_2$, and —CO—NH-$A_3$;

Y is selected from —O—, —S—, —NH—, and —$CH_2$—; alternatively, Y is absent, being a single bond;

Z is selected from —H, —COOH, —COOEt, —$NH_2$, —NH-$A_1$, —NH—CO-$A_2$, and —CO—NH-$A_4$;

$A_1$, $A_2$, $A_3$ and $A_4$ are independently any substituent.

In some embodiments of the present invention, the present invention further provides use of a compound having a structure as shown in formula II in the preparation of a tumor imaging agent:

Formula II

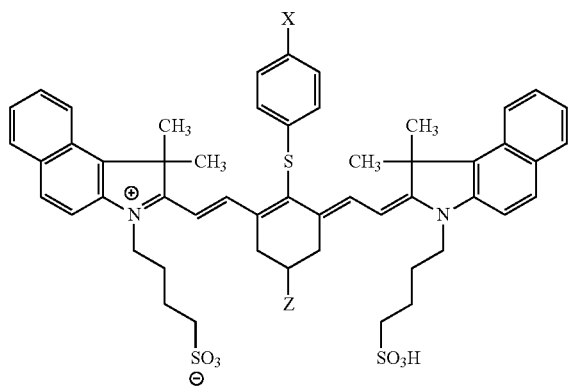

wherein X is any one of —H, —COOH, —$NH_2$, and —CO—NH-$A_3$;

Z is any one of —H, —COOH, —COOEt, —$NH_2$, and —CO—NH-$A_4$;

$A_3$ is peptide, saccharide or folic acid derivative;

$A_4$ is —$C_6H_5$, DOTA, DTPA, peptide, saccharide or folic acid derivative.

In other embodiments of the present invention, the present invention further provides use of a compound having a structure as shown in any one of formula IV to formula X in the preparation of a tumor imaging agent:

Formula V

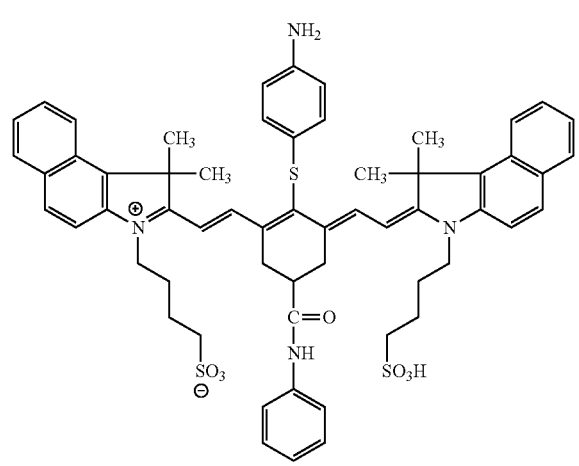

Formula VI

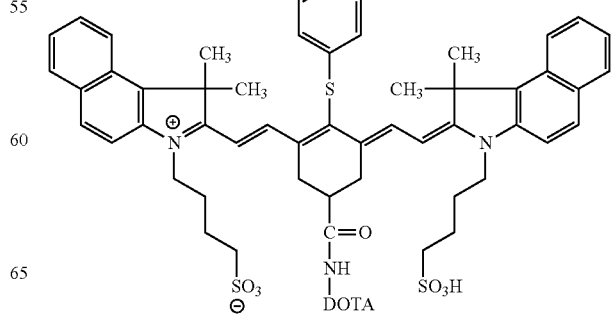

-continued

Formula VII
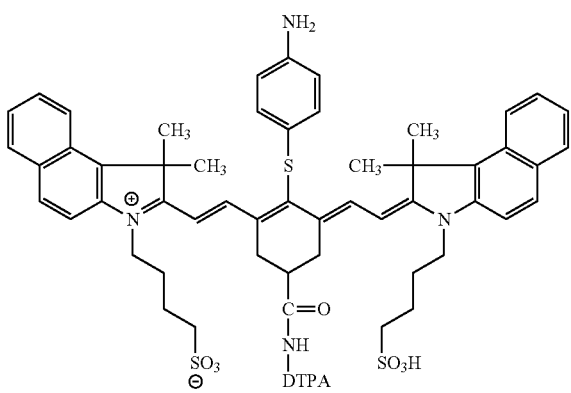

Formula VIII
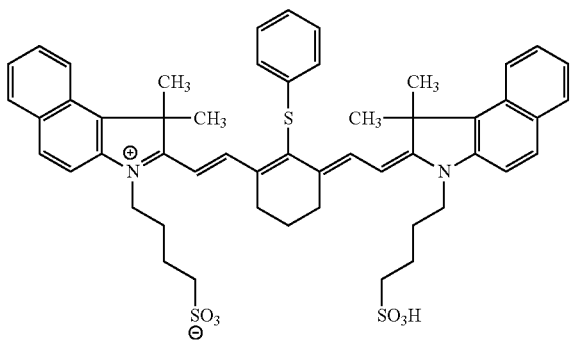

Formula IX
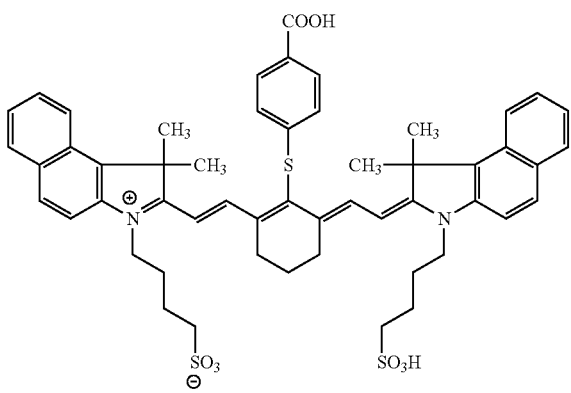

Formula X
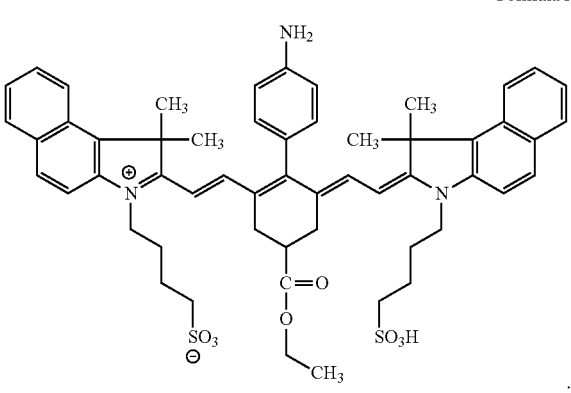

The present invention further provides use of a compound having a structure as shown in formula XI in the preparation of a dual-function agent for tumor imaging and tumor treatment:

Formula XI
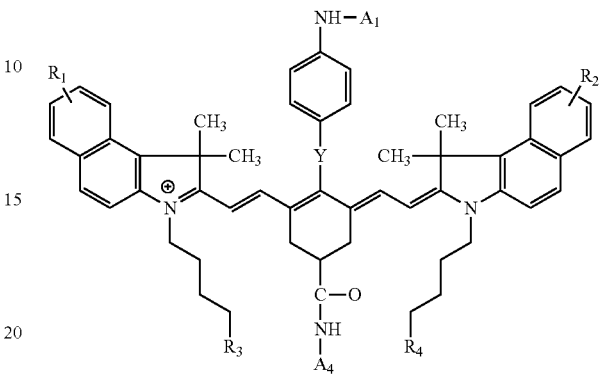

wherein Y is O, S, —NH—, or —CH$_2$—; alternatively, Y is absent, being a single bond;

$R_1$ and $R_2$ are independently selected from hydrogen, alkaryl, fluorinated groups or sulfonated groups;

$R_3$ and $R_4$ are independently selected from —H, —SO$_3$H, —SO$_3$Na, —COOH, —OH or —NH$_2$;

$A_1$ is -$A_5$-$A_6$, —H, maleimide, or a maleimide analogue substituted with F-18 or I-124, in which $A_5$ is carbonyl, alkyl or an aryl chain; $A_6$ is maleimide, a maleimide analogue substituted with F-18 or I-124, peptide, saccharide, folic acid, tetrapyrrole ring or reduced tetrapyrrole ring;

$A_4$ is —(CH$_2$)$_n$-PS, in which n=0 to 6; and PS is glycosyl, tetrapyrrole ring or reduced tetrapyrrole ring, RGD peptide, iRGD peptide, DOTA, DTPA or triamino ester;

preferably, the tetrapyrrole ring includes, but is not limited to, chlorin, bacteriochlorin, purpurin imide and rhodopurpurin imide.

In other embodiments of the present invention, use of a compound having a structure as shown in formula XII in the preparation of a dual-function agent for tumor imaging and tumor treatment is further provided:

Formula XII
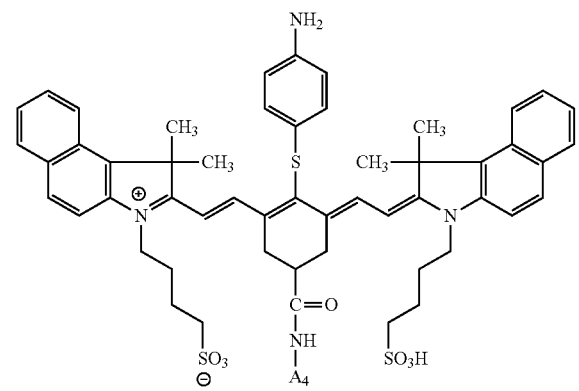

wherein $A_4$ is RGD peptide, iRGD peptide, glycosyl, DTPA, DOTA, triamino ester or —(CH$_2$)$_n$-PS in which n=0 to 6, and PS has a structure as shown in formula XIII, formula XIV or formula XV;

Formula XIII

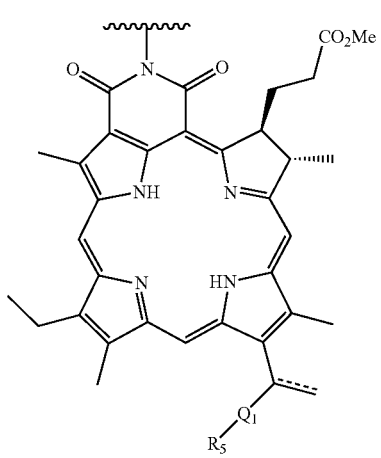

Formula XIV

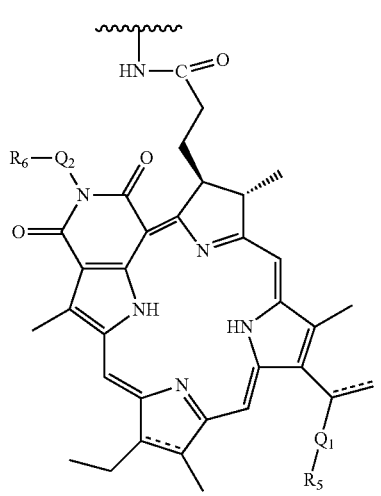

Formula XV

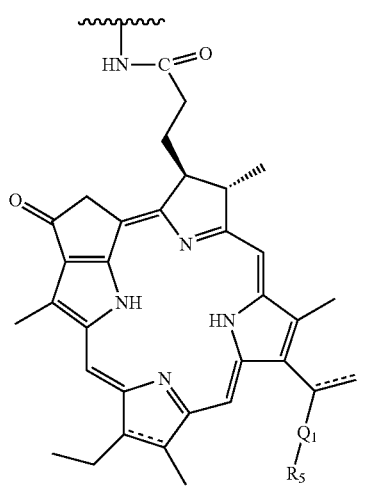

Formula XVI

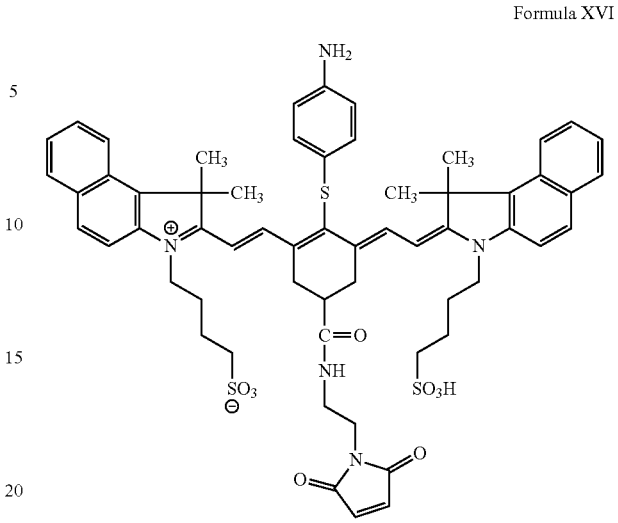

Formula XVII

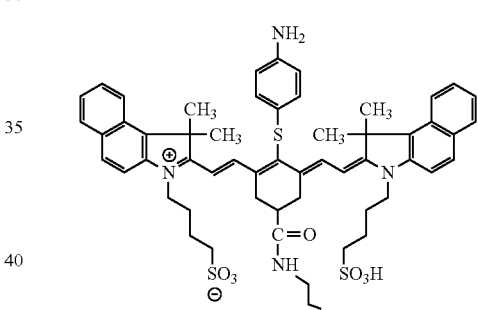

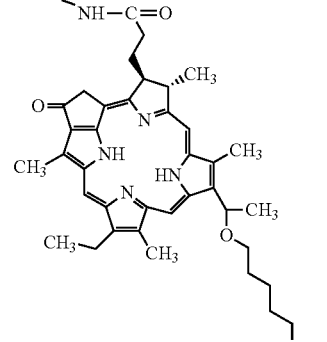

wherein --- represents a single bond or a double bond; $Q_1$ and $Q_2$ are independently —O—, alkyl, aryl or reduced aryl;

$R_5$ and $R_6$ are independently alkyl or alkyl labelled with F-18, iodobenzyl or iodobenzyl labelled with I-124.

In other embodiments of the present invention, use of a compound having a structure as shown in formula XVI or formula XVII in the preparation of a dual-function agent for tumor imaging and tumor treatment is further provided:

The present invention introduces a structure of p-aminothioether into the compound and allows conjugation at 2''' position. Due to formation of a stable conjugated system at the 2''' position, reactive oxygen will be more easily formed under irradiation, so that the effect for tumor to absorb the photosensitizer is greatly increased.

The present invention provides use of an intermediate having a structure as shown in any one of formula XVIII to formula XXII in the preparation of a tumor imaging agent and/or in the preparation of a dual-function agent for tumor imaging and tumor treatment:

Formula XVIII

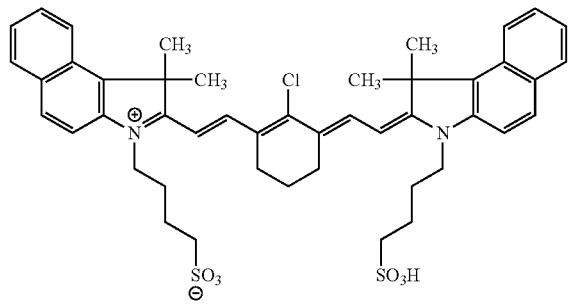

Formula XIX

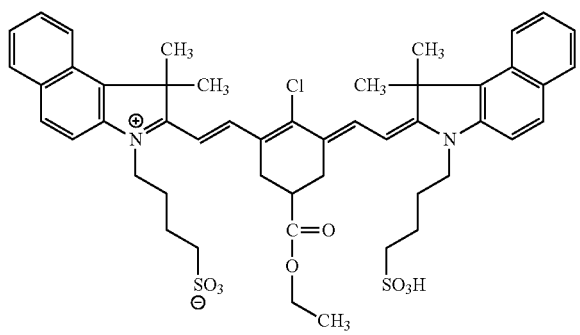

Formula XX

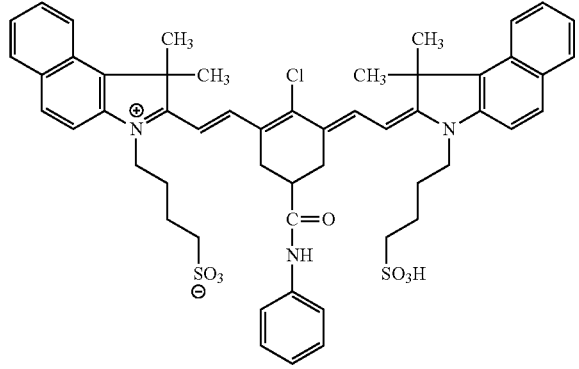

Formula XXI

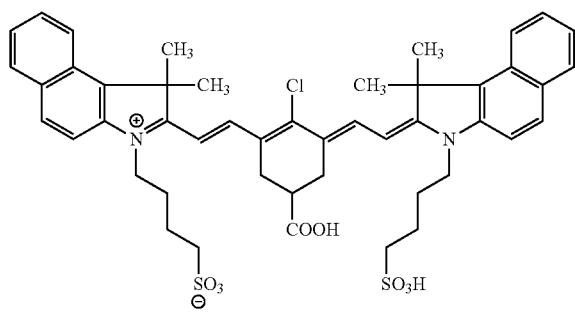

Formula XXII

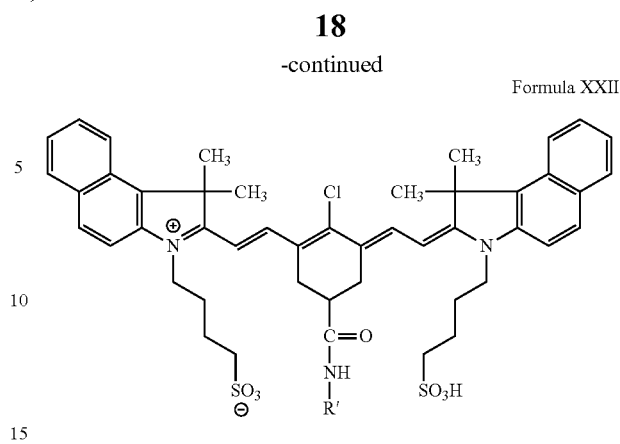

wherein R' is any one of —$C_6H_5$, maleimide, a maleimide analogue with or without I-124 and/or F-18, tetrapyrrole group with or without I-124 and/or F-18, tetrapyrrole ring, reduced tetrapyrrole ring, RGD peptide, iRGD peptide, glycosyl, DOTA, DTPA, and triamino ester;

preferably, the tetrapyrrole ring includes, but is not limited to, chlorin, bacteriochlorin, purpurin imide and rhodopurpurin imide.

The present invention provides a preparation method for an intermediate having a structure as shown in formula XVIII, formula XIX or formula XX, comprising steps of:

step 1: subjecting a compound having a structure as shown in formula XXIII to a first Vilsmeier-Haack-Arnold reaction in the presence of phosphoryl chloride, DMF and aniline, to produce a compound having a structure as shown in formula XXIV; and step 2: subjecting the compound having the structure as shown in formula XXIV to a first substitution reaction with a compound having a structure shown in formula XXV, to obtain the intermediate;

Formula XVIII

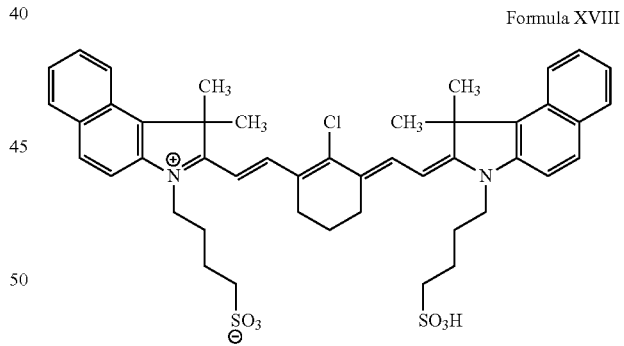

Formula XIX

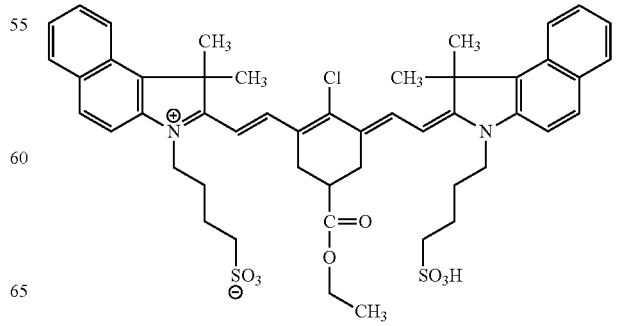

-continued

Formula XX

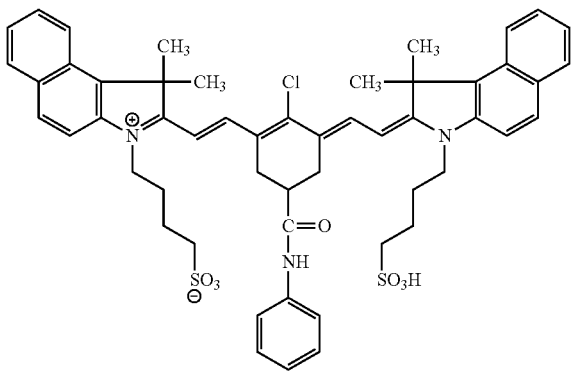

Formula XXIII

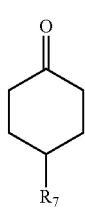

Formula XXIV

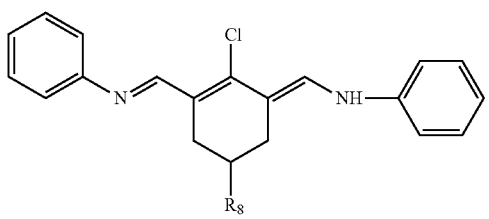

Formula XXV

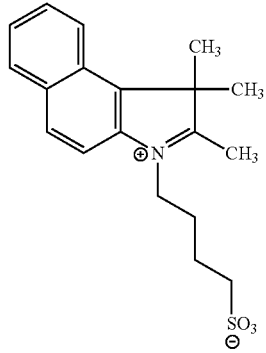

wherein $R_7$ is selected from —H,

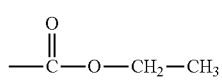

or —COOH; and $R_8$ is selected from —H,

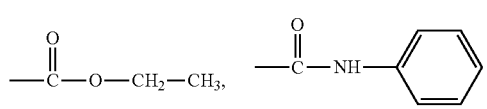

or —COOH.

The present invention further provides a preparation method for an intermediate having a structure as shown in formula XXI, comprising steps of:

step 1: subjecting 4-carboxyl cyclohexanone to a second Vilsmeier-Haack-Arnold reaction in the presence of phosphoryl chloride and DMF, to produce a compound having a structure as shown in formula XXVI; and step 2: subjecting the compound having the structure as shown in formula XXVI to a second substitution reaction with a compound having a structure shown in formula XXV, to obtain the intermediate;

Formula XXI

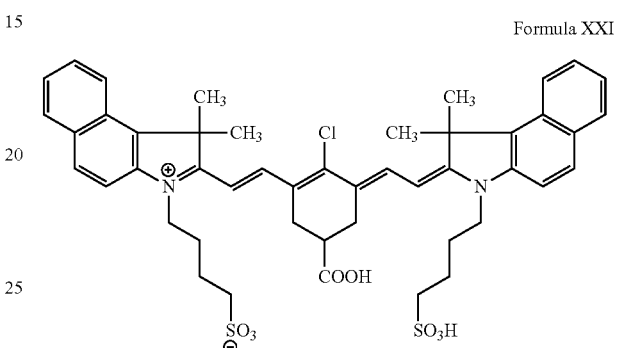

Formula XXVI

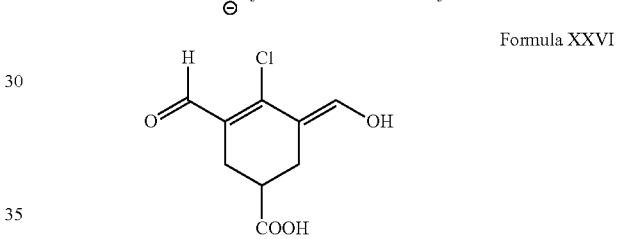

Formula XXV

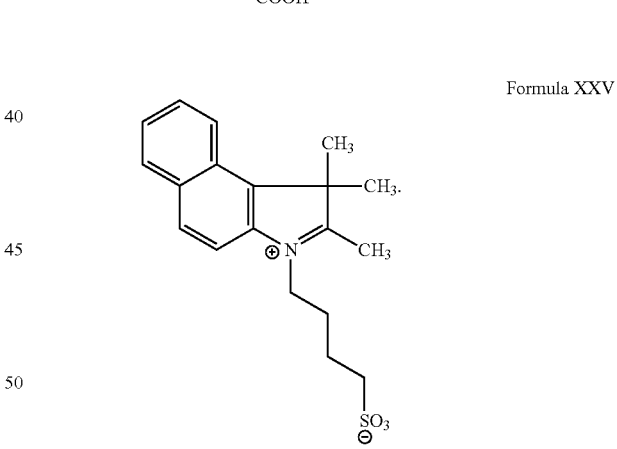

Preferably, after Step 2, the preparation method for an intermediate having a structure as shown in formula XXI further comprises: subjecting the intermediate having the structure as shown in formula XXI to a third substitution reaction with R'—$NH_2$ in the presence of BOP and DMF, to produce an intermediate having a structure shown in formula XXII;

wherein R' is maleimide, a maleimide analogue, tetrapyrrole ring or reduced tetrapyrrole ring;

preferably, the tetrapyrrole ring includes, but is not limited to, chlorin, bacteriochlorin, purpurin imide and rhodopurpurin imide;

Formula XXI

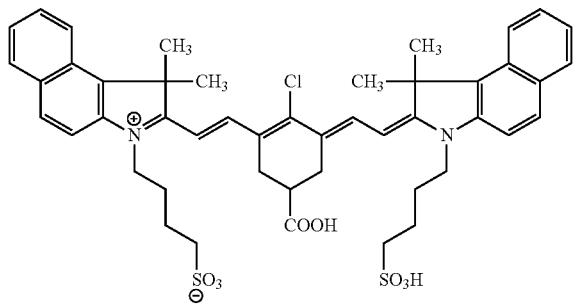

Formula XXII

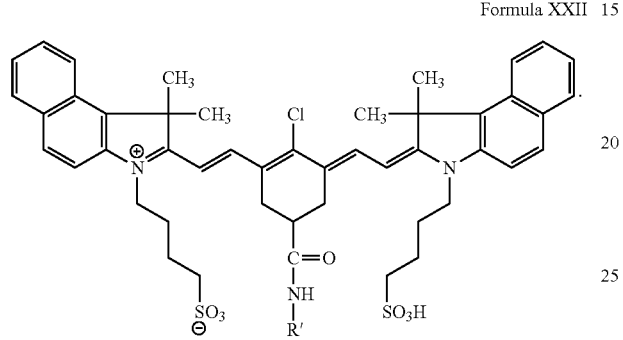

The present invention further provides a preparation method for a compound having a structure as shown in formula III, formula IV, formula V, formula VIII or formula IX, comprising steps of:

step 1: subjecting a compound having a structure as shown in formula XXIII to a first Vilsmeier-Haack-Arnold reaction in the presence of phosphoryl chloride, DMF and aniline, to produce a compound having a structure as shown in formula XXIV;

step 2: subjecting the compound having the structure as shown in formula XXIV to a first substitution reaction with a compound having a structure shown in formula XXV, to produce an intermediate having a structure as shown in formula XVIII, formula XIX or formula XX; and Step 3: subjecting the intermediate having the structure shown in formula XVIII, formula XIX or formula XX to a fourth substitution reaction with a compound having a structure shown in formula XXVII, respectively, to obtain the compound having the structure as shown in formula III, formula IV, formula V, formula VIII or formula IX;

Formula III

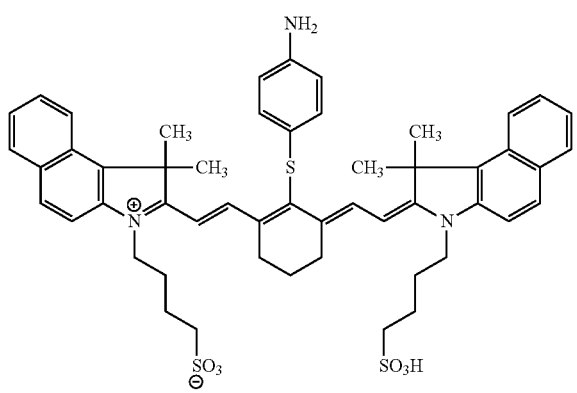

Formula IV

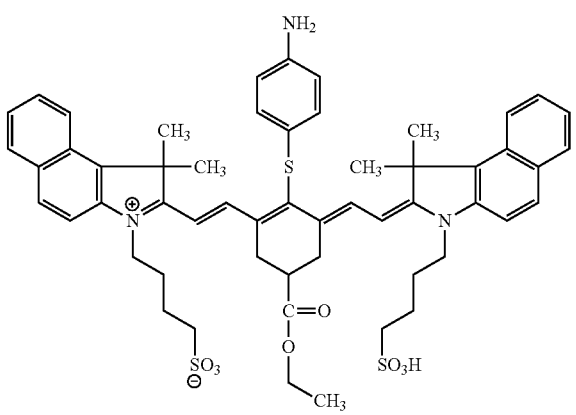

Formula V

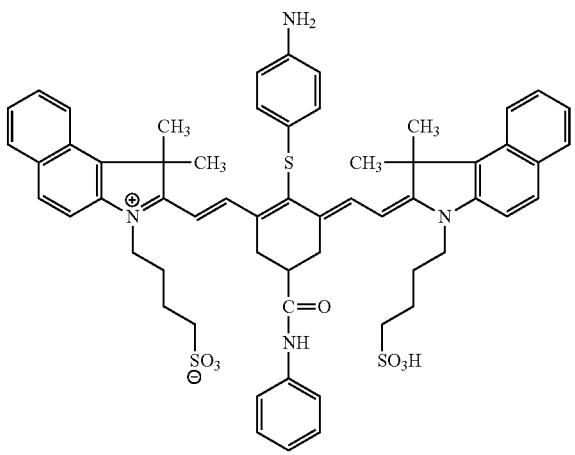

Formula VIII

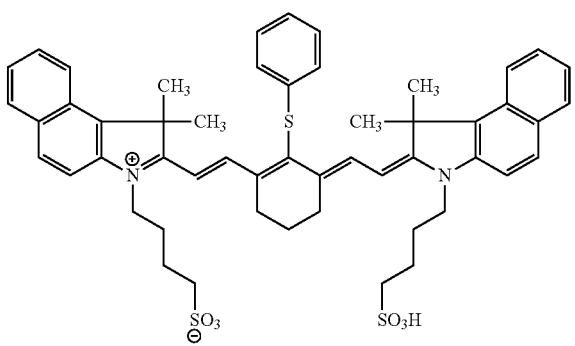

Formula IX

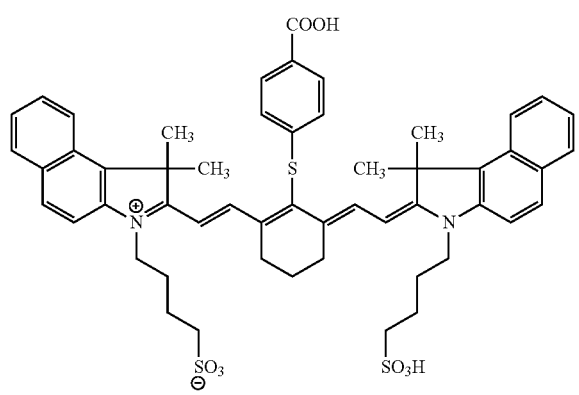

Formula XVIII

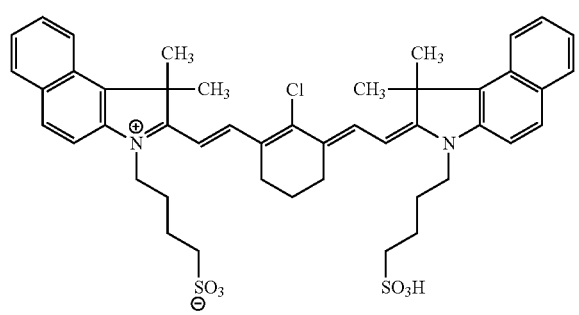

Formula XIX

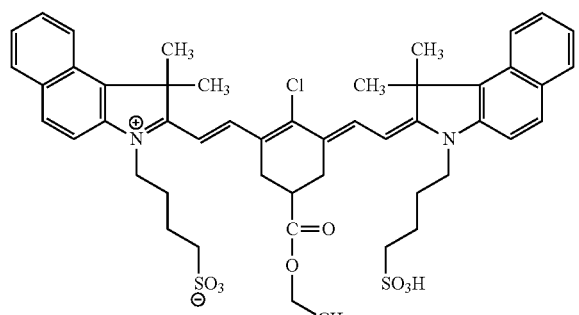

Formula XX

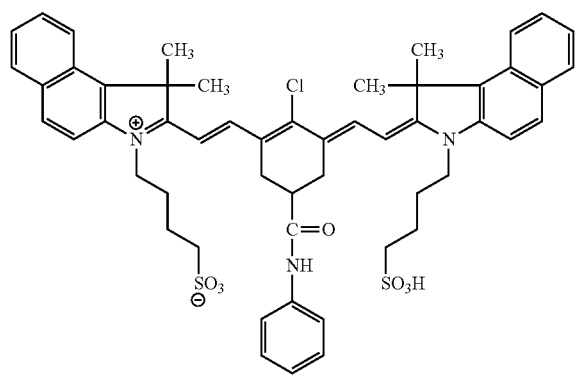

Formula XXIII

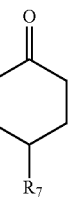

Formula XXIV

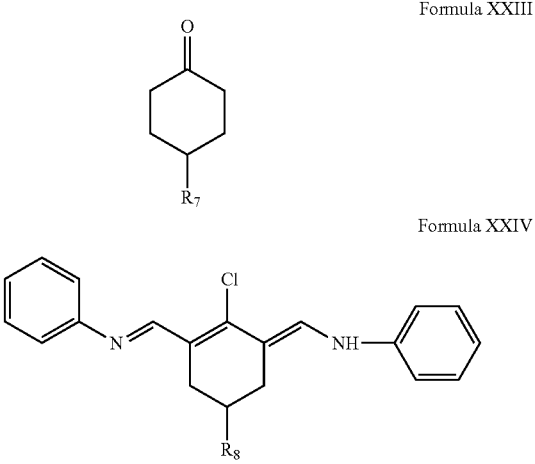

Formula XXV

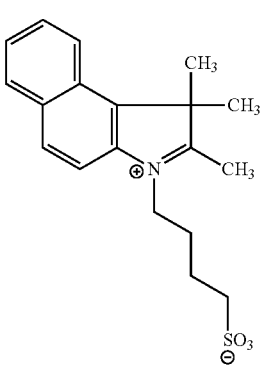

Formula XXVII

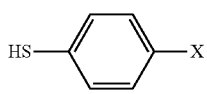

wherein $R_7$ is selected from —H,

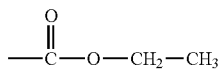

or —COOH; $R_8$ is selected from —H,

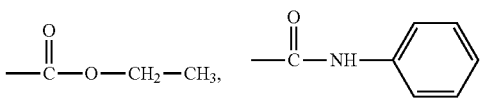

or —COOH; and X is selected from —H, —COOH or —NH$_2$.

The present invention further provides a preparation method for a compound having a structure as shown in formula X, comprising steps of:

step 1: subjecting a compound having a structure as shown in formula XXIII to a third Vilsmeier-Haack-Arnold reaction in the presence of phosphoryl chloride, DMF and aniline, to produce a compound having a structure as shown in formula XXIV;

step 2: subjecting the compound having the structure as shown in formula XXIV to a fifth substitution reaction with a compound having a structure as shown in formula XXV, to produce an intermediate having a structure as shown in formula XIX; and step 3: subjecting the intermediate having the structure shown in formula XIX to a sixth substitution reaction with 4-aminophenylboronic acid under the catalysis of Pd(PPh$_3$)$_4$, to obtain the compound having the structure as shown in formula X;

Formula X

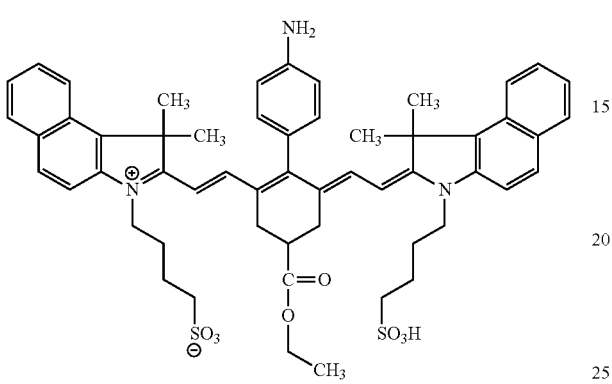

Formula XIX

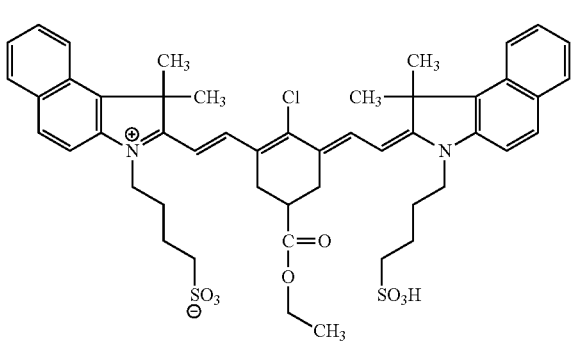

Formula XXIII

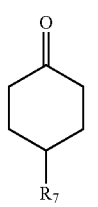

Formula XXIV

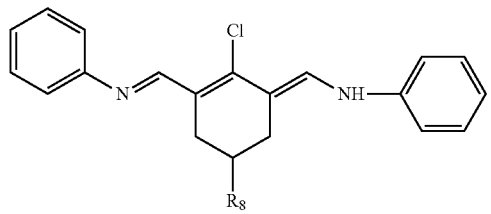

Formula XXV

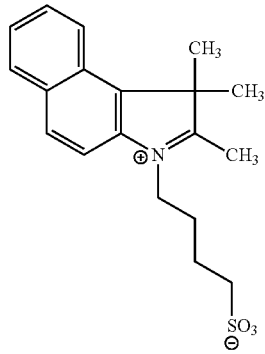

wherein R$_7$ is —COOH; and R$_8$ is

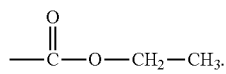

The present invention further provides a preparation method for a compound having a structure as shown in formula VI, formula VII or formula XVII, comprising steps of:

step 1: subjecting 4-carboxyl cyclohexanone to a second Vilsmeier-Haack-Arnold reaction in the presence of phosphoryl chloride and DMF, to produce a compound having a structure as shown in formula XXVI;

step 2: subjecting the compound having the structure as shown in formula XXVI to a second substitution reaction with a compound having a structure shown in formula XXV, to produce an intermediate having a structure shown in formula XXI;

step 3: subjecting the intermediate having the structure as shown in formula XXI to a third substitution reaction with a compound having a structure shown in formula XXVIII, DOTA-NH$_2$ or DTPA-NH$_2$ in the presence of BOP and DMF, to produce an intermediate having a structure shown in formula XXIX, formula XXX or formula XXXI; and step 4: subjecting the intermediate having the structure shown in formula XXIX, formula XXX or formula XXXI to a seventh substitution reaction with 4-aminothiophenol, to obtain the compound having the structure as shown in formula VI, formula VII or formula XVII;

Formula XXVI

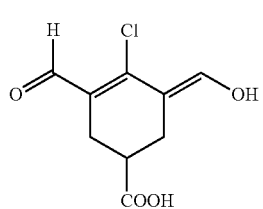

Formula XXV
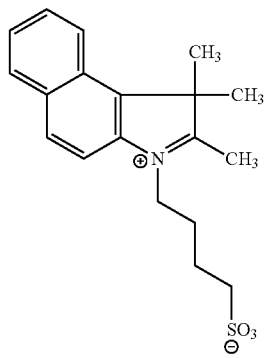
Formula XXI
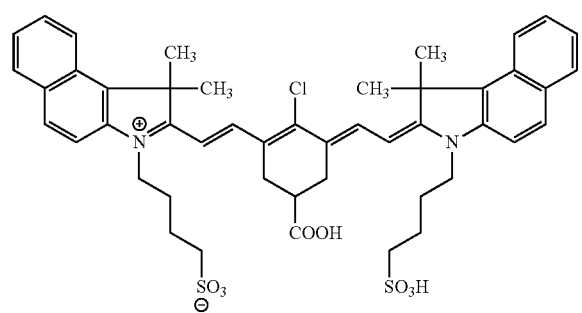
Formula XXVIII
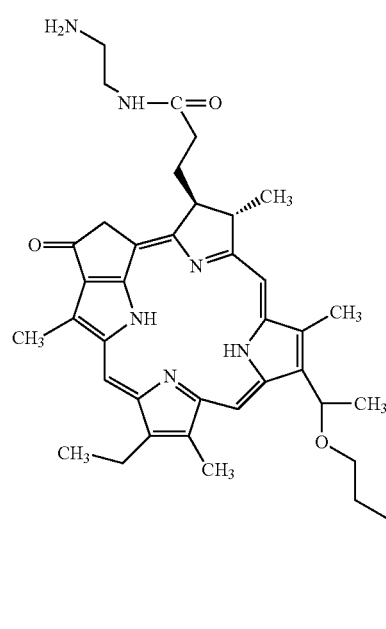
Formula XXIX
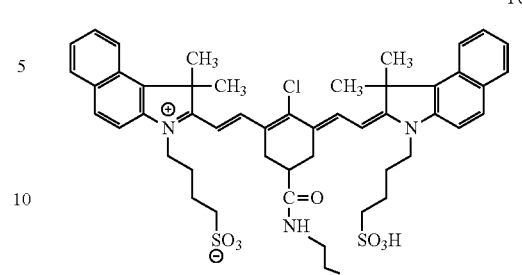
Formula XXX
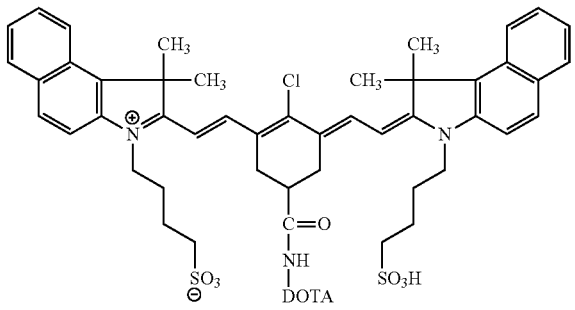
Formula XXXI
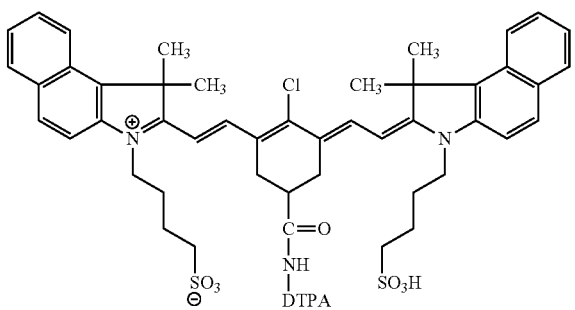

Formula VI

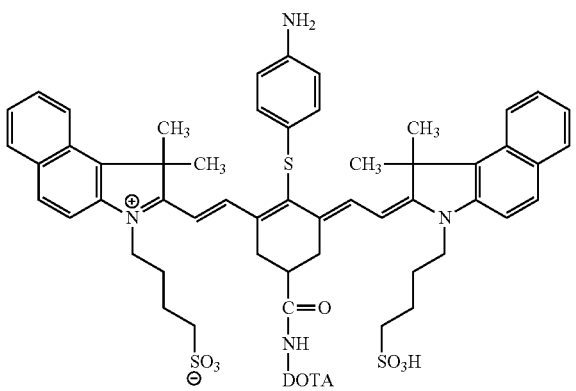

Formula VII

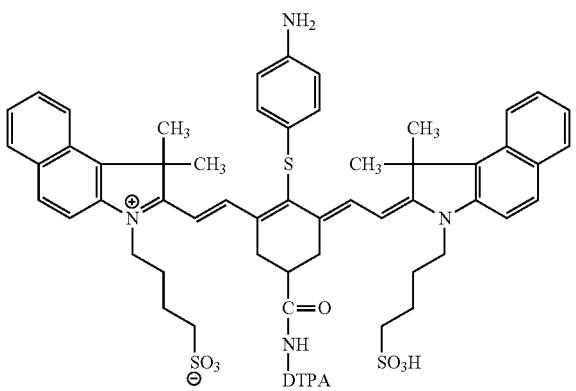

Formula XVII

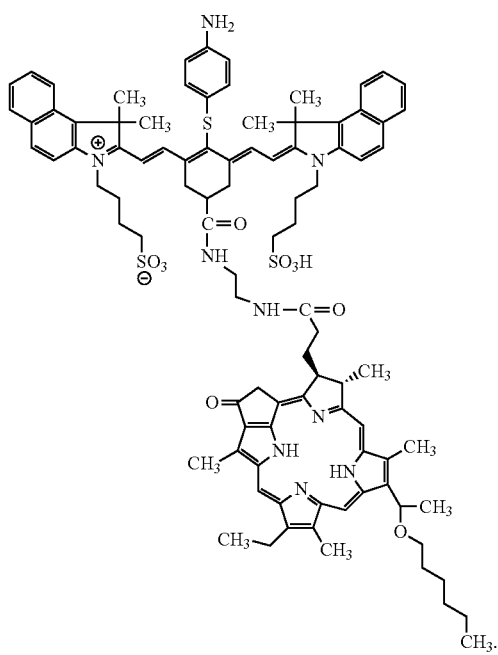

Compared with the prior art, the present invention provides a cyanine dye compound and preparation method thereof, a dual-function agent for photodynamic therapy and preparation method thereof. The cyanine dye compound provided according to the present invention is bond to multiple markers, and the introduction of those markers allows the cyanine dye compound to be capable of accurately binding to the multiple target molecules in tumor cells. The target molecules include: αvβ3 integrin, folic acid, saccharide or the like which are only highly expressed in tumor cells or activated endothelial cells. Due to the increased accuracy in the binding of the dye to tumor cells, the cyanine dye provided according to the present invention can effectively reduce the background value when used as an imaging agent for tumor imaging, and avoid excessive residues in the liver. Moreover, the compound provided according to the present invention allows the cyanine dye compound to be conjugated at 2''' position with a photosensitizer, forming a cyanine dye-photosensitizer conjugate. Due to the presence of the conjugated system, the absorption effect of tumor to such a conjugate is greatly increased, thus improving the killing capability of the conjugate to tumor cells when it is used as a dual-function agent in photodynamic therapy. In addition, since the cyanine dye portion in the conjugate provided in the present invention may be bond with multiple target molecules in tumor cells; the application range of the dual-function agent is expanded. Experiments show that: when used as an imaging agent, the cyanine dye compound provided according to the present invention is capable of better binding to tumor cells, making the imaging background purer; and the liver exhibits low absorption efficiency to the cyanine dye provided in the present invention. Furthermore, the dual-function agent provided in the present invention may be useful for imaging and treatment of a variety of tumors such as lung, colon tumor, etc., and exhibits good imaging and therapeutic effect.

BRIEF DESCRIPTION OF THE DRAWINGS

FIG. 1 shows electronic absorption spectra for compounds having a structure shown in formula VIII, formula IX, formula III, formula IV, formula V and formula X, in which: curve 1 shows the electronic absorption spectrum of the compound having a structure of formula VIII; curve 2 shows the electronic absorption spectrum of the compound having a structure of formula IX; curve 3 shows the electronic absorption spectrum of the compound having a structure of formula III; curve 4 shows the electronic absorption spectrum of the compound having a structure of formula IV; curve 5 shows the electronic absorption spectrum of the compound having a structure of formula V; and curve 6 shows the electronic absorption spectrum of the compound having a structure of formula X.

FIG. 2 shows whole-body imaging of mice which have been injected an intermediate having a structure of formula XVIII, in which FIG. 2(a) shows whole-body imaging of mouse 1 in the experiment 4 hours after being injected into an intermediate having a structure of formula XVIII; FIG. 2(b) shows whole-body imaging of mouse 1 in the experiment 8 hours after being injected into an intermediate having a structure of formula XVIII; FIG. 2(c) shows whole-body imaging of mouse 1 in the experiment 12 hours after being injected into an intermediate having a structure of formula XVIII; FIG. 2(d) shows whole-body imaging of mouse 1 in the experiment 24 hours after being injected into an intermediate having a structure of formula XVIII; FIG. 2(e) shows whole-body imaging of mouse 1 in the experiment 48 hours after being injected into an intermediate having a structure of formula XVIII; FIG. 2(f) shows whole-body imaging of mouse 1 in the experiment 72 hours after being injected into an intermediate having a structure of formula XVIII; FIG. 2(g) shows whole-body imaging of mouse 1 in the experiment 96 hours after being injected into an intermediate having a structure of formula XVIII; FIG. 2(h)

shows whole-body imaging of mouse 2 in the experiment 4 hours after being injected into an intermediate having a structure of formula XVIII; FIG. 2(i) shows whole-body imaging of mouse 2 in the experiment 8 hours after being injected into an intermediate having a structure of formula XVIII; FIG. 2(j) shows whole-body imaging of mouse 2 in the experiment 12 hours after being injected into an intermediate having a structure of formula XVIII; FIG. 2(k) shows whole-body imaging of mouse 2 in the experiment 24 hours after being injected into an intermediate having a structure of formula XVIII; FIG. 2(l) shows whole-body imaging of mouse 2 in the experiment 48 hours after being injected into an intermediate having a structure of formula XVIII; FIG. 2(m) shows whole-body imaging of mouse 2 in the experiment 72 hours after being injected into an intermediate having a structure of formula XVIII; FIG. 2(n) shows whole-body imaging of mouse 2 in the experiment 96 hours after being injected into an intermediate having a structure of formula XVIII; FIG. 2(o) shows whole-body imaging of mouse 3 in the experiment 4 hours after being injected into an intermediate having a structure of formula XVIII; FIG. 2(p) shows whole-body imaging of mouse 3 in the experiment 8 hours after being injected into an intermediate having a structure of formula XVIII; FIG. 2(q) shows whole-body imaging of mouse 3 in the experiment 12 hours after being injected into an intermediate having a structure of formula XVIII; FIG. 2(r) shows whole-body imaging of mouse 3 in the experiment 24 hours after being injected into an intermediate having a structure of formula XVIII; FIG. 2(s) shows whole-body imaging of mouse 3 in the experiment 48 hours after being injected into an intermediate having a structure of formula XVIII; FIG. 2(t) shows whole-body imaging of mouse 3 in the experiment 72 hours after being injected into an intermediate having a structure of formula XVIII; and FIG. 2(u) shows whole-body imaging of mouse 3 in the experiment 96 hours after being injected into an intermediate having a structure of formula XVIII in the experiment.

FIG. 3 shows whole-body imaging of mice which have been injected into a compound having a structure of formula III, in which FIG. 3(a) shows whole-body imaging of mouse 1 4 hours after being injected into a compound having a structure of formula III; FIG. 3(b) shows whole-body imaging of mouse 1 in the experiment 8 hours after being injected into a compound having a structure of formula III; FIG. 3(c) shows whole-body imaging of mouse 1 in the experiment 12 hours after being injected into a compound having a structure of formula III; FIG. 3(d) shows whole-body imaging of mouse 1 in the experiment 24 hours after being injected into a compound having a structure of formula III; FIG. 3(e) shows whole-body imaging of mouse 1 in the experiment 48 hours after being injected into a compound having a structure of formula III; FIG. 3(f) shows whole-body imaging of mouse 1 in the experiment 72 hours after being injected into a compound having a structure of formula III; FIG. 3(g) shows whole-body imaging of mouse 1 in the experiment 96 hours after being injected into a compound having a structure of formula III; FIG. 3(h) shows whole-body imaging of mouse 2 in the experiment 4 hours after being injected into a compound having a structure of formula III; FIG. 3(i) shows whole-body imaging of mouse 2 in the experiment 8 hours after being injected into a compound having a structure of formula III; FIG. 3(j) shows whole-body imaging of mouse 2 in the experiment 12 hours after being injected into a compound having a structure of formula III; FIG. 3(k) shows whole-body imaging of mouse 2 in the experiment 24 hours after being injected into a compound having a structure of formula III; FIG. 3(l) shows whole-body imaging of mouse 2 in the experiment 48 hours after being injected into a compound having a structure of formula III; FIG. 3(m) shows whole-body imaging of mouse 2 in the experiment 72 hours after being injected into a compound having a structure of formula III; FIG. 3(n) shows whole-body imaging of mouse 2 in the experiment 96 hours after being injected into a compound having a structure of formula III; FIG. 3(o) shows whole-body imaging of mouse 3 in the experiment 4 hours after being injected into a compound having a structure of formula III; FIG. 3(p) shows whole-body imaging of mouse 3 in the experiment 8 hours after being injected into a compound having a structure of formula III; FIG. 3(q) shows whole-body imaging of mouse 3 in the experiment 12 hours after being injected into a compound having a structure of formula III; FIG. 3(r) shows whole-body imaging of mouse 3 in the experiment 24 hours after being injected into a compound having a structure of formula III; FIG. 3(s) shows whole-body imaging of mouse 3 in the experiment 48 hours after being injected into a compound having a structure of formula III; FIG. 3(t) shows whole-body imaging of mouse 3 in the experiment 72 hours after being injected into a compound having a structure of formula III; and FIG. 3(u) shows whole-body imaging of mouse 3 in the experiment 96 hours after being injected into a compound having a structure of formula III in the experiment.

FIG. 4 shows whole-body imaging of mice which have been injected into a compound having a structure of formula IV, in which FIG. 4(a) shows whole-body imaging of mouse 1 in the experiment 4 hours after being injected into a compound having a structure of formula IV; FIG. 4(b) shows whole-body imaging of mouse 1 in the experiment 8 hours after being injected into a compound having a structure of formula IV; FIG. 4(c) shows whole-body imaging of mouse 1 in the experiment 12 hours after being injected into a compound having a structure of formula IV; FIG. 4(d) shows whole-body imaging of mouse 1 in the experiment 24 hours after being injected into a compound having a structure of formula IV; FIG. 4(e) shows whole-body imaging of mouse 1 in the experiment 48 hours after being injected into a compound having a structure of formula IV; FIG. 4(f) shows whole-body imaging of mouse 1 in the experiment 72 hours after being injected into a compound having a structure of formula IV; FIG. 4(g) shows whole-body imaging Of mouse 1 in the experiment 96 hours after being injected into a compound having a structure of formula IV; FIG. 4(h) shows whole-body imaging of mouse 2 in the experiment 4 hours after being injected into a compound having a structure of formula IV; FIG. 4(i) shows whole-body imaging of mouse 2 in the experiment 8 hours after being injected into a compound having a structure of formula IV; FIG. 4(j) shows whole-body imaging of mouse 2 in the experiment 12 hours after being injected into a compound having a structure of formula IV; FIG. 4(k) shows whole-body imaging of mouse 2 in the experiment 24 hours after being injected into a compound having a structure of formula IV; FIG. 4(l) shows whole-body imaging of mouse 2 in the experiment 48 hours after being injected into a compound having a structure of formula IV; FIG. 4(m) shows whole-body imaging of mouse 2 in the experiment 72 hours after being injected into a compound having a structure of formula IV; FIG. 4(n) shows whole-body imaging of mouse 2 in the experiment 96 hours after being injected into a compound having a structure of formula IV; FIG. 4(o) shows whole-body imaging of mouse 3 in the experiment 4 hours after being injected into a compound having a structure of formula IV; FIG. 4(p) shows whole-body imaging of mouse 3 in the experiment 8 hours after being injected into a compound having a structure of formula IV; FIG. 4(q) shows whole-body imaging of mouse 3 in the experiment 12 hours after being injected into a compound having a structure of formula IV; FIG. 4(r) shows whole-body imaging of mouse 3 in the experiment 24 hours after being injected into a compound having a structure of formula IV; FIG. 4(s) shows whole-body imaging of mouse 3 in the experiment 48 hours after being injected into a compound having a structure of formula IV; FIG. 4(t) shows whole-body imaging of mouse 3 in the experiment 72 hours after being injected into a compound having a structure of formula IV; and FIG. 4(u) shows whole-body imaging of mouse 3 in the experiment 96 hours after being injected into a compound having a structure of formula IV in the experiment.

FIG. 5 shows whole-body imaging of mice which have been injected into a compound having a structure of formula V, in which FIG. 5(a) shows whole-body imaging of mouse 1 in the experiment 4 hours after being injected into a compound having a structure of formula V; FIG. 5(b) shows whole-body imaging of mouse 1 in the experiment 8 hours after being injected into a compound having a structure of formula V; FIG. 5(c) shows whole-body imaging of mouse 1 in the experiment 12 hours after being injected into a compound having a structure of formula V; FIG. 5(d) shows whole-body imaging of mouse 1 in the experiment 24 hours after being injected into a compound having a structure of formula V; FIG. 5(e) shows whole-body imaging of mouse 1 in the experiment 48 hours after being injected into a compound having a structure of formula V; FIG. 5(f) shows whole-body imaging of mouse 1 in the experiment 72 hours after being injected into a compound having a structure of formula V; FIG. 5(g) shows whole-body imaging of mouse 1 in the experiment 96 hours after being injected into a compound having a structure of formula V; FIG. 5(h) shows whole-body imaging of mouse 2 in the experiment 4 hours after being injected into a compound having a structure of formula V; FIG. 5(i) shows whole-body imaging of mouse 2 in the experiment 8 hours after being injected into a compound having a structure of formula V; FIG. 5(j) shows whole-body imaging of mouse 2 in the experiment 12 hours after being injected into a compound having a structure of formula V; FIG. 5(k) shows whole-body imaging of mouse 2 in the experiment 24 hours after being injected into a compound having a structure of formula V; FIG. 5(l) shows whole-body imaging of mouse 2 in the experiment 48 hours after being injected into a compound having a structure of formula V; FIG. 5(m) shows whole-body imaging of mouse 2 in the experiment 72 hours after being injected into a compound having a structure of formula V; and FIG. 5(n) shows whole-body imaging of mouse 2 in the experiment 96 hours after being injected into a compound having a structure of formula V.

FIG. 8 shows imaging effects for the compound having a structure shown in formula XVII as a dual-function agent for tumor imaging and tumor treatment, in which FIG. 8(a) shows whole-body imaging of a mouse without being injected into a compound having imaging function; FIG. 8(b) shows whole-body imaging of mouse 1 in the experiment 24 hours after being injected into a compound having a structure of formula XVII; FIG. 8(c) shows whole-body imaging of mouse 2 in the experiment 24 hours after being injected into a compound having a structure as shown in formula XVII; and FIG. 8(d) shows whole-body imaging of mouse 3 in the experiment 24 hours after being injected into a compound having a structure as shown in formula XVII in the experiment.

FIG. 9 shows comparison of absorption effects for the compound having a structure of formula III provided according to the present invention as a dual-function agent for tumor imaging and tumor treatment in the liver of a mouse with and without tumor cells, respectively.

DETAILED DESCRIPTION

Figure 3:
Figure 3:
Figure 3:

The present invention provides a cyanine dye compound and preparation method thereof, and a dual-function agent for photodynamic therapy and preparation method thereof. In view of the disclosure herein, those skilled in the art can realize it by properly modifying the process parameters. It should be particularly noted that, all similar substitutions and alterations are obvious for those skilled in the art, which would be considered to fall within the present invention. The method and application of the present invention have been described by means of preferred examples, and obviously, for those skilled in the art, modifications or proper alterations can be made to the method and application of the present invention by those skilled in the art to achieve and apply the technology of the present invention, without departing from the content, spirit and scope of the present invention.

Reagents used in the present invention may all be commercially available.

The present invention will be further illustrated with reference to examples as follows.

EXAMPLE 1

Preparation of an Intermediate Having a Structure Shown in Formula XVIII

The preparation procedure thereof is shown in the scheme below:

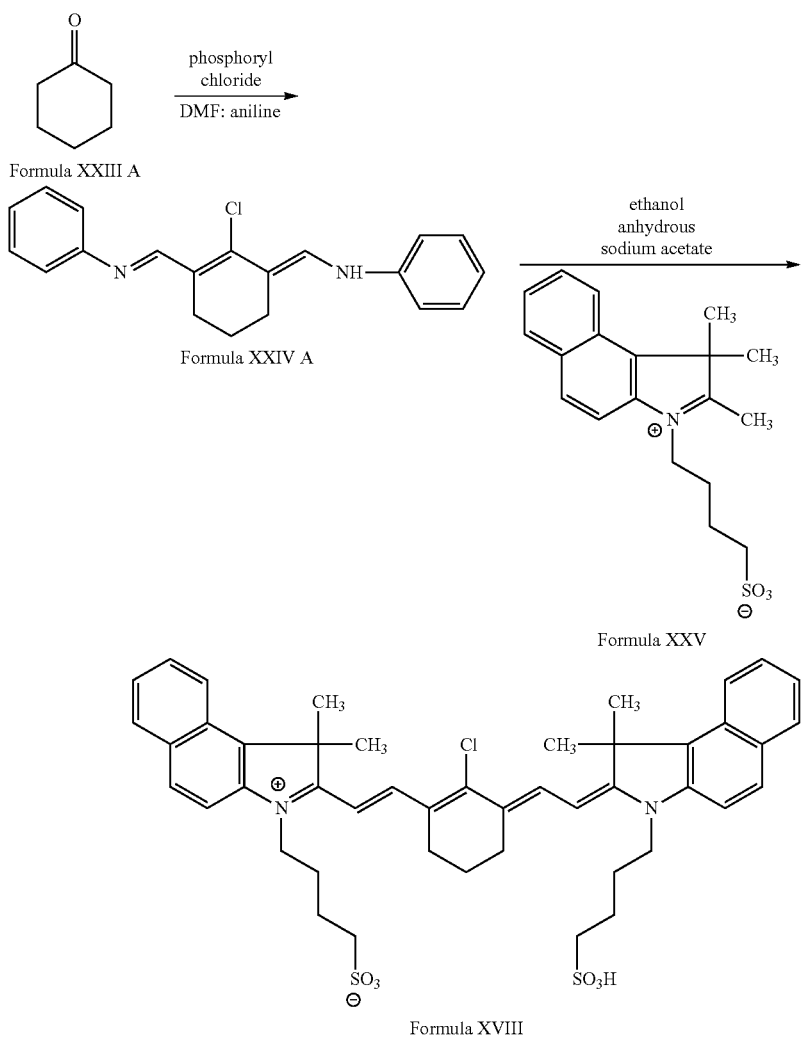

At 0° C., to a 10 ml solution comprising 1 mmol N,N-dimethylformide (DMF) in dichloromethane, 1 mmol phosphoryl chloride was slowly added dropwise under stirring, and continued to be stirred for 1 hour. 2 mmol cyclohexanone (a compound shown in formula XXIII A, corresponding to the compound shown in formula XXIII in which the substituent is —H) was added, followed by heating under reflux for 1 hour, cooled down and added thereto a mixed solution of aniline and ethanol (1:1 in volume ratio), and continued to be stirred for 30 minutes. The resulting solution was poured into a mixture of crushed ice and concentrated hydrochloric acid (1:1 in volume ratio), and refrigerated at a temperature of 4° C. overnight. After filtration, the precipitate was washed with cold water and diethyl ether, and finally dried under reduced pressure, resulting in a compound having a structure as shown in formula XXIV A (corresponding to the compound shown in formula XXIV in which the substituent is —H), with a yield of 45%.

2 mmol of the compound having a structure as shown in formula XXIV A (corresponding to the compound shown in formula XXIV in which the substituent $R^8$ is —H), 1 mmol of a compound having a structure as shown in formula XXV and 4 mmol anhydrous sodium acetate were dissolved in 25 ml of anhydrous ethanol, and then the resulting mixed solution was stirred at room temperature overnight in nitrogen atmosphere. The solvent was removed by rotary evaporation, and diethyl ether was added dropwise into the resulting residues until precipitate was generated. The precipitate was further purified by silica gel column chromatography with a mixed solution of dichloromethane and methanol (9:1 in volume ratio) as an eluent, resulting in an intermediate having a structure shown in formula XVIII, with a yield of 42%.

EXAMPLE 2

Preparation of Intermediates Having a Structure Shown in Formula XIX and Formula XX The preparation procedure thereof is shown in the scheme below:

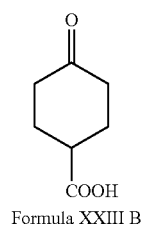

Formula XXIII B

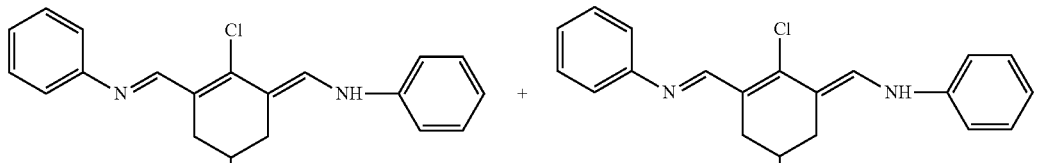

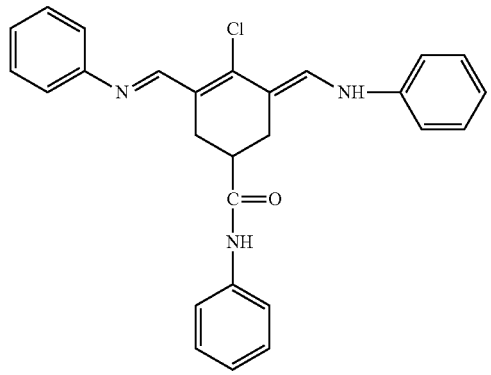

Formula XXIV B

Formula XXIV C

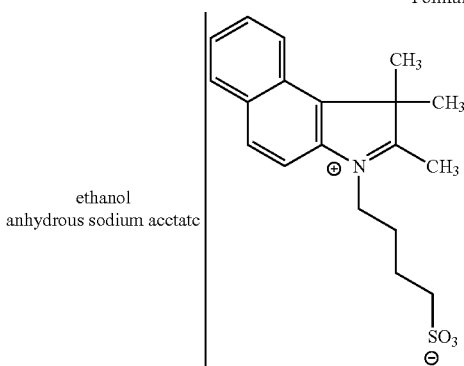

Formula XXV

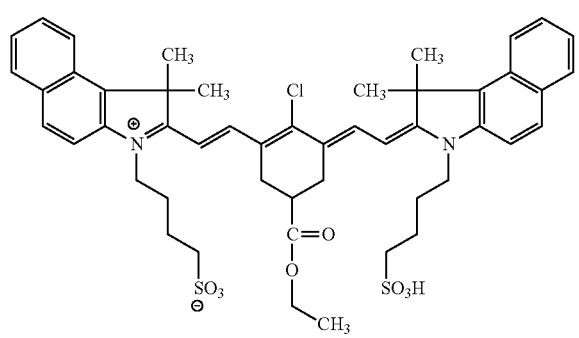

Formula XIX

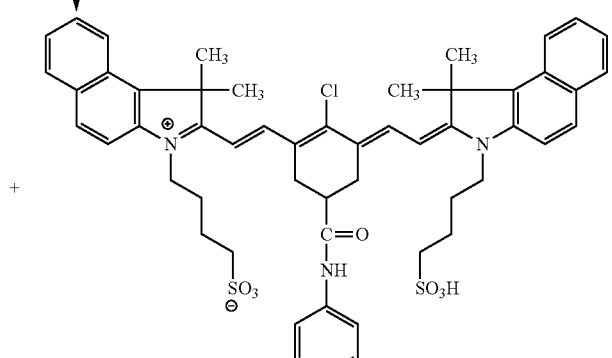

Formula XX

At 0° C., to a 10 ml solution comprising 1 mmol N,N-dimethylformide (DMF) in dichloromethane, 1 mmol phosphoryl chloride was slowly added dropwise under stirring, and continued to be stirred for 1 hour. 2 mmol 4-hydroxy-cyclohexanone (a compound shown in formula XXIII B, corresponding to the compound shown in formula XXIII in which the substituent $R^7$ is —COOH) was added, followed by heating under reflux for 1 hour, cooled down and added thereto a mixed solution of aniline and ethanol (1:1 in volume ratio), and continued to be stirred for 30 minutes. The resulting solution was poured into a mixture of crushed ice and concentrated hydrochloric acid (1:1 in volume ratio), and refrigerated at a temperature of 4° C. overnight. After filtration, the precipitate was washed with cold water and diethyl ether, and finally dried under reduced pressure, resulting in a compound having a structure as shown in formula XXIV B (corresponding to a compound shown in formula XXIV in which the substituent $R^8$ is —COOH), and a compound shown in XXIV C (corresponding to a compound shown in formula XXIV in which the substituent $R^8$ is

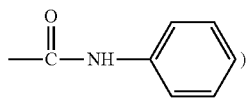)

with a yield of 45%.

2 mmol of the resulting compound having a structure as shown in formula XXIV B (corresponding to the compound shown in formula XXIV in which the substituent $R^8$ is —COOH), a compound having a structure shown in formula XXIV C (corresponding to the compound shown in formula XXIV in which the substituent $R^8$ is

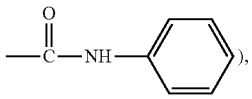), 1 mmol of a compound having a structure as shown in formula XXV and 4 mmol anhydrous sodium acetate were dissolved in 25 ml of anhydrous ethanol, and then the resulting mixed solution was stirred at room temperature overnight in nitrogen atmosphere. The solvent was removed by rotary evaporation, and diethyl ether was added dropwise into the resulting residues until precipitate was generated. The precipitate was further purified by silica gel column chromatography with a mixed solution of dichloromethane and methanol (9:1 in volume ratio) as an eluent, resulting in a main product which was an intermediate having a structure shown in formula XIX, with a yield of 42%. A by-product, which was an intermediate having the structure shown in formula XX, was obtained with a yield of 22% as elution proceeded.

The intermediate having the structure shown in formula XX was detected, with a result as follows:

UV-vis max (in MeOH): 820 nm; 1HNMR (400 MHz, CD3OD): δ 8.60 (d, 2H, J=14 Hz), 8.26 (d, 2H, J=10 Hz), 7.99 (m, 4H), 7.62-7.69 (m, 5H), 7.49 (t, 2H, J=7.2 Hz), 7.32 (t, 2H, J=7.2 Hz), 7.10 (m, 1H), 6.43 (d, 2H, J=14 Hz), 4.35 (t, 4H, J=7.6 Hz), 3.22 (dd, 1H, J=4, 12 Hz), 2.82-3.00 (m, 8H), 1.87-2.15 (m, 22H). EIMS (m/z): 991 (M++2Na).

EXAMPLE 3

Preparation of an Intermediate Having a Structure Shown in Formula XIX

The preparation procedure thereof is shown in the scheme below:

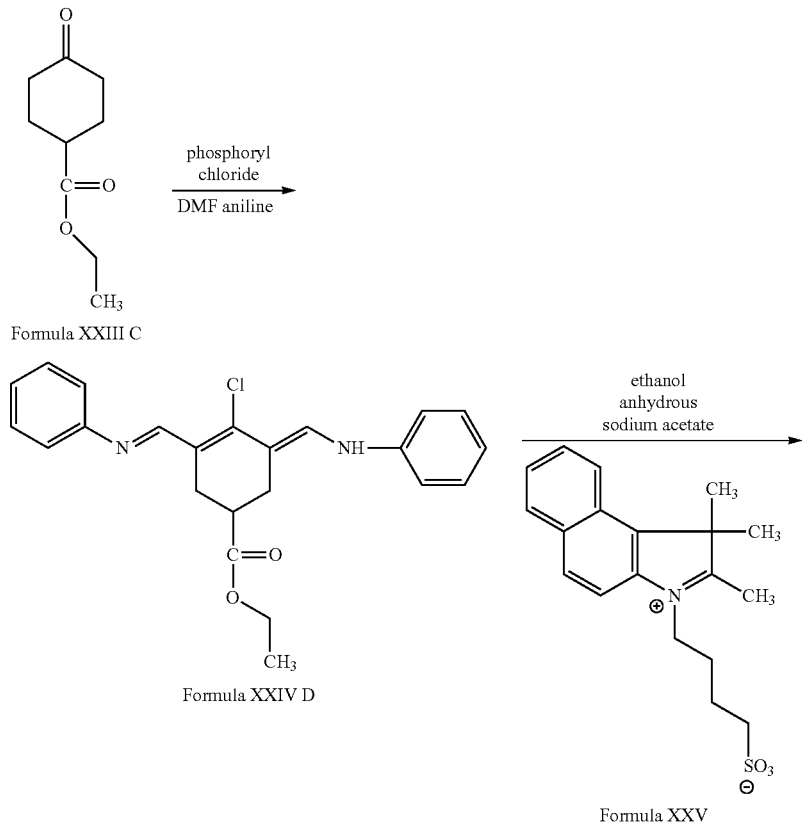

-continued

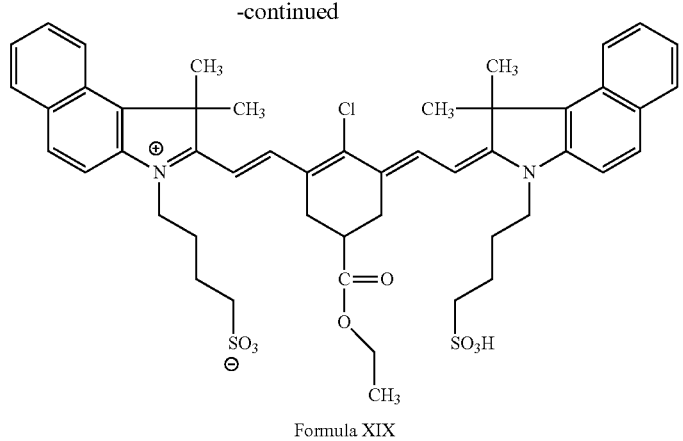

Formula XIX

At 0° C., to a 10 ml solution comprising 1 mmol N,N-dimethylformide (DMF) in dichloromethane, 1 mmol phosphoryl chloride was slowly added dropwise under stirring, and continued to be stirred for 1 hour. 2 mmol 4-methyl acetate cyclohexanone (a compound shown in formula XXIII C, corresponding to the compound shown in formula XXIV in which the substituent $R^7$ is

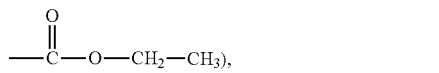

was added, followed by heating under reflux for 1 hour, cooled down and added with a mixed solution of aniline and ethanol (1:1 in volume ratio), and continued to be stirred for 30 minutes. The resulting solution was poured into a mixture of crushed ice and concentrated hydrochloric acid (1:1 in volume ratio), and refrigerated at a temperature of 4° C. overnight. After filtration, the precipitate was washed with cold water and diethyl ether, and finally dried under reduced pressure, resulting in a compound having a structure as shown in formula XXIV D (corresponding to the compound shown in formula XXIV in which the substituent $R^8$ is

—C(=O)—O—CH$_2$—CH$_3$), with a yield of 43%.

2 mmol of the compound having a structure as shown in formula XXIV D (corresponding to the compound shown in formula XXIV in which the substituent $R^8$ is

—C(=O)—O—CH$_2$—CH$_3$), 1 mmol or a compound having a structure as shown in formula XXV and 4 mmol anhydrous sodium acetate were dissolved in 25 ml of anhydrous ethanol, and then the resulting mixed solution was stirred at room temperature overnight in nitrogen atmosphere. The solvent was removed by rotary evaporation, and diethyl ether was added dropwise into the resulting residues until precipitate was generated. The precipitate was further purified by silica gel column chromatography with a mixed solution of dichloromethane and methanol (9:1 in volume ratio) as an eluent, resulting in a main product which was an intermediate having the structure shown in formula XIX, with a yield of 42%.

EXAMPLE 4

Preparation of an Intermediate Having a Structure as Shown in Formula XXI

The preparation process thereof is shown in the scheme below:

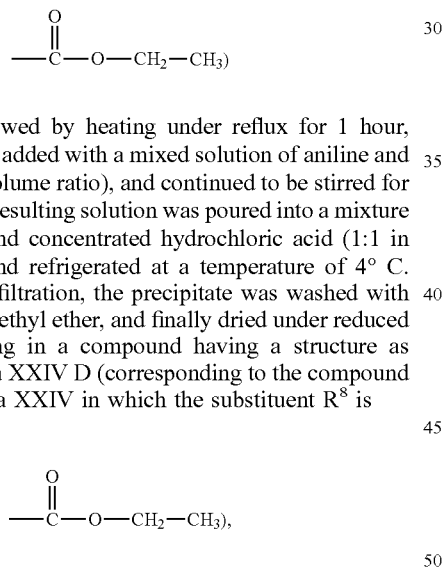

Formula XXIII B

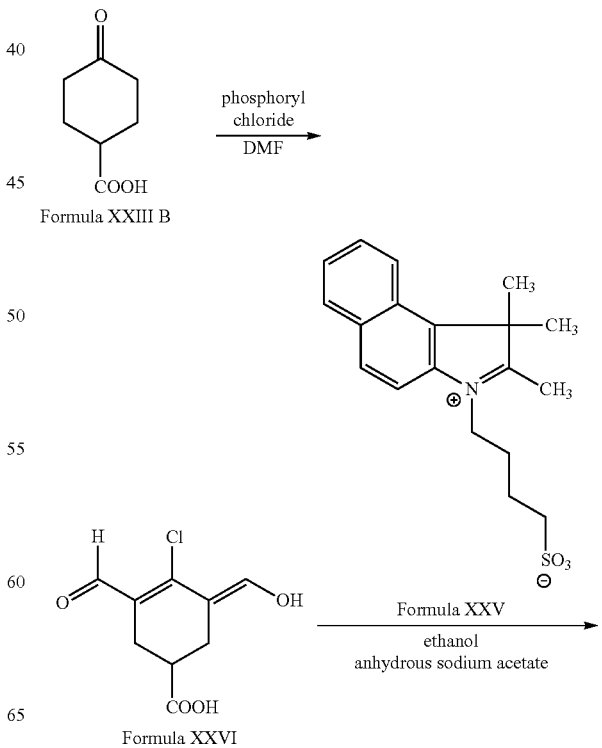

Formula XXVI Formula XXV

-continued

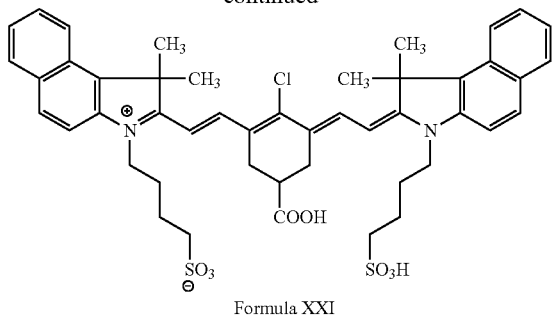

Formula XXI

At 0° C., to a 10 ml solution comprising 1 mmol N,N-dimethylformide (DMF) in dichloromethane, 1 mmol phosphoryl chloride was slowly added dropwise under stirring, and continued to be stirred for 1 hour. 2 mmol 4-hydroxycyclohexanone (a compound shown in formula XXIII B, corresponding to the compound shown in formula XXIII in which the substituent $R^7$ is —COOH) was added, followed by heating under reflux for 1 hour, cooled down and added thereto a mixed solution of aniline and ethanol (1:1 in volume ratio), and continued to be stirred for 30 minutes. The resulting solution was poured into a mixture of crushed ice and concentrated hydrochloric acid (1:1 in volume ratio), and refrigerated at a temperature of 4° C. overnight. After filtration, the precipitate was washed with cold water and diethyl ether, and finally dried under reduced pressure, resulting in a compound having a structure as shown in formula XXVI, with a yield of 48%.

2 mmol of the compound having a structure as shown in formula XXVI and 1 mmol of a compound having a structure as shown in formula XXV were dissolved in anhydrous DMF, and then the resulting mixed solution was stirred at room temperature for 24 hours in nitrogen atmosphere. The solvent was removed by rotary evaporation, and diethyl ether was dropwise added into the resulting residues until precipitate was generated. The precipitate was further purified by silica gel column chromatography with a mixed solution of dichloromethane and methanol (9:1 in volume ratio) as an eluent, resulting in a main product which was an intermediate having the structure shown in formula XXI, with a yield of 42%.

The intermediate having the structure as shown in formula XXI was detected, with a result as follows:

UV-vis max (in MeOH): 820 nm, 1 HNMR (400 MHz, CD$_3$OD): δ 8.55 (d, 2H, J=14 Hz), 8.26 (d, 2H, J=8.4 Hz), 8.02 (d, 2H, J=10.8 Hz), 7.98 (d, 2H, J=8.4 Hz), 7.79 (d, 2H, J=9.2 Hz), 7.63 (dt, 2H, J=8.4, 1.2 Hz), 7.48 (dt, 2H, J=7.6, 0.8 Hz), 6.41 (d, 2H, J=14 Hz), 4.37 (t, 4H, J=7.2 Hz), 3.15-3.18 (m, 2H), 2.90 (t, 4H, J=7.6 Hz), 2.67-2.76 (m, 3H), 2.08-2.12 (m, 4H), 2.03 (s, 12H), 1.96-2.00 (m, 4H). EIMS (m/z): 915 (M$^-$+2Na).

EXAMPLE 5

Preparation of a Compound Having a Structure Shown in Formula VIII

A 20 ml solution comprising 10 mmol thiophenol and 1 mmol of the intermediate having a structure shown in formula XVIII prepared in EXAMPLE 1 of the present invention in anhydrous DMF was stirred at room temperature and in nitrogen atmosphere for 12 hours. The solvent was removed by rotary evaporation. The precipitate was washed with diethyl ether, and further purified by silica gel column chromatography with a mixed solution of dichloromethane and methanol (9:1 in volume ratio) as an eluent, resulting in the compound having a structure shown in formula VIII, with a yield of 78%.

The compound provided according to the present invention was detected, with a result as follows:

UV-vis max (in MeOH): 831 nm: 1HNMR (400 MHz, CD$_3$OD): δ 8.89 (d, 2H, J=14 Hz), 8.14 (d, 2H, J=14 Hz), 7.95 (t, 4H, J=9.2 Hz), 7.56-7.62 (m, 4H), 7.44 (t, 2H, J=7.2 Hz), 7.28-7.34 (m, 4H), 7.10-7.12 (m, 1H), 6.36 (d, 2H, J=14 Hz), 4.24 (t, 4H, J=7.6 Hz), 2.82-2.94 (m, 8H), 1.93-2.10 (m, 1014), 1.78 (s, 12H). EIMS (m/z): 945 (M$^+$+2Na).

EXAMPLE 6

Preparation of a Compound Having a Structure Shown in Formula IX

A 20 ml solution comprising 10 mmol 4-carboxyl thiophenol and 1 mmol of the intermediate having a structure shown in formula XVIII prepared in EXAMPLE 1 of the present invention in anhydrous DMF was stirred at room temperature and in nitrogen atmosphere for 12 hours. The solvent was removed by rotary evaporation. The precipitate was washed with diethyl ether, and further purified by silica gel column chromatography with a mixed solution of dichloromethane and methanol (9:1 in volume ratio) as an eluent, resulting in a compound having the structure shown in formula IX, with a yield of 83%.

The compound provided according to the present invention was detected, with a result as follows:

UV-vis max (in MeOH): 837 nm, 1HNMR (400 MHz, CD$_3$OD): δ 8.87 (d, 2H, J=14 Hz), 8.15 (d, 2H, J=14 Hz), 7.91-7.99 (m, 6H), 7.57-7.63 (m, 4H), 7.44 (t, 2H, J=7.2 Hz), 7.36 (d, 2H, J=8.4 Hz), 6.40 (d, 2H, J=14 Hz), 4.27 (t, 4H, J=7.6 Hz), 2.85-2.92 (m, 8H), 1.93-2.10 (m, 10H), 1.77 (s, 12H). EIMS (m/z): 989 (M$^+$+2Na).

EXAMPLE 7

Preparation of a Compound Having a Structure Shown in Formula IV

A 20 ml solution comprising 10 mmol 4-aminothiophenol and 1 mmol of the intermediate having a structure shown in formula XIX prepared in EXAMPLE 2 of the present invention in anhydrous DMF was stirred at room temperature and in nitrogen atmosphere for 12 hours. The solvent was removed by rotary evaporation. The precipitate was washed with diethyl ether, and further purified by silica gel column chromatography with a mixed solution of dichloromethane and methanol (9:1 in volume ratio) as an eluent, resulting in a compound having the structure shown in formula IV, with a yield of 73%.

The compound having the structure shown in formula IV provided in the present invention was detected, with a result as follows:

UV-vis$_{max}$ (in MeOH): 829 nm, $^1$HNMR (400 MHz, CD$_3$OD): δ 9.00 (d, 2H, J=14 Hz), 8.22 (d, 2H, J=14 Hz), 7.91-8.02 (m, 4H), 7.58-7.63 (m, 4H), 7.44 (t, 2H, J=7.2 Hz), 7.10 (d, 2H, J=8.4 Hz), 6.62 7.10 (d, 2H, J=8.4 Hz), 6.38 (d, 2H, J=14 Hz), 4.34 (t, 4H, J=7.6 Hz), 4.22 (q, 2H, J=8.0 Hz), 2.82-2.94 (m, 2H), 1.95-2.08 (m, 10H), 1.85 & 1.82 (s, 12H), 1.24 (t, 3H, J=7.2 Hz). EIMS (m/z): 1032 (M$^-$+2Na).

EXAMPLE 8

Preparation of a Compound Having a Structure Shown in Formula V

A 20 ml solution comprising 10 mmol 4-aminothiophenol and 1 mmol of the intermediate having a structure shown in formula XX prepared in EXAMPLE 2 or 3 of the present invention in anhydrous DMF was stirred at room temperature and in nitrogen atmosphere for 12 hours. The solvent was removed by rotary evaporation. The precipitate was washed with diethyl ether, and further purified by silica gel column chromatography with a mixed solution of dichloromethane and methanol (9:1 in volume ratio) as an eluent, resulting in a compound having the structure shown in formula V, with a yield of 77%.

The compound having the structure shown in formula V provided in the present invention was detected, with a result as follows:

UV-vis$_{max}$ (in MeOH): 825 nm, $^1$HNMR (400 MHz, CD$_3$OD): δ 9.02 (d, 2H, J=14 Hz), 8.18 (d, 2H, J=8.4 Hz), 8.02 (d, 2H, J=10.8 Hz), 7.97 (t, 2H, J=8.4 Hz), 7.67 (d, 2H, J=9.2 Hz), 7.60-7.63 (m, 4H), 7.48 (dt, 2H, J=7.6, 0.8 Hz), 7.32 (t, 2H, J=7.6 Hz), 7.14 (d, 2H, J=8.8 Hz), 6.68 (d, 2H, J=8.8 Hz), 6.39 (d, 2H, J=14 Hz), 4.29 (t, 4H, J=7.2 Hz), 3.15-3.21 (m, 2H), 2.80-2.96 (m, 3H), 2.85 (t, 4H, J=7.6 Hz), 1.92-2.12 (m, 4H), 1.98 (s, 6H), 1.83 (s, 6H). EIMS (m/z): 1079 (M$^-$+2Na).

EXAMPLE 9

Preparation of a Compound Having a Structure Shown in Formula X 1.8 mmol 4-aminophenylboronic acid and 1 mmol of an intermediate having a structure shown in formula XX prepared in EXAMPLE 2 or 3 of the present invention were dissolved with water, followed by addition of 0.065 mmol Pd(PPh$_3$)$_4$. The resulting solution was heated under reflux for 12 hours for reaction, and the reaction process was monitored by UV-VIS spectroscopy. When the intermediate having the structure shown in formula XX was reacted completely, the reaction was stopped. The reaction solution was cooled to room temperature, and removed water under vacuum. It was precipitated with diethyl ether, and the precipitate was further purified by silica gel column chromatography with a mixed solution of dichloromethane and methanol (9:1 in volume ratio) as an eluent, resulting in the compound having the structure shown in formula X, with a yield of 48%.

The compound having the structure shown in formula X provided in the present invention was detected, with a result as follows:

UV-vis max (in MeOH): 787 nm, 1HNMR (400 MHz, CDCl$_3$): 8.07 (d, 2H, J=8.0 Hz), 7.94 (t, 4H, J=8.0 Hz), 7.53-7.61 (m, 6H), 7.40-7.44 (m, 2H), 6.98-7.01 (m, 4H), 6.23 (d, 2H, J=12 Hz), 4.21-4.27 (t, 6H), 3.02-3.05 (m, 4H), 2.86-2.92 (m, 6H), 1.90-2.03 (m, 10H), 1.59 (s, 12H), 1.27-1.32 (m, 3H). EIMS (m/z): 1000 (M$^-$+2Na).

EXAMPLE 10

Preparation of a Compound Having a Structure Shown in Formula XXII 0.11 mmol of an intermediate having a structure shown in formula XXI prepared in EXAMPLE 4 of the present invention, 0.074 mmol of N-(2-aminoethyl)maleimide trifluoroacetate and 0.11 mmol of benzotriazol-1-yloxytri(dimethylamino)phosphonium hexafluorophosphate (BOP) were dissolved in anhydrous DMF to obtain a reaction solution. The above reaction solution was stirred at room temperature and in argon atmosphere for 12 hours. After completion of the reaction (monitored by TLC), the solvent was removed by suction filtration under reduced pressure, and the resulting crystals were washed with diethyl ether, to result in a product. The resulting product was further purified by preparative silica gel TLC with a mixed solution of dichloromethane and methanol (95:5 in volume ratio) as an eluent, resulting in a compound having a structure shown in formula XXII, with a yield of 44% when R' in the structure shown in formula XXII is maleimide.

The compound having the structure shown in formula XXII with R' being maleimide provided in the present invention was detected, with a result as follows:

UV-vis max (in MeOH): 820 nm, 1HNMR (400 MHz, CD$_3$OD): δ 8.54 (d, 2H, J=14 Hz), 8.27 (d, 2H, J=8.4 Hz), 8.03 (d, 2H, J=10.8 Hz), 7.99 (d, 2H, J=8.4 Hz), 7.68 (d, 2H, J=9.2 Hz), 7.63 (dt, 2H, J=8.4, 1.2 Hz), 7.49 (dt, 2H, J=7.6, 0.8 Hz), 6.89 (s, 2H), 6.45 (d, 2H, J=14 Hz), 4.40 (t, 4H, J=7.2 Hz), 3.68-3.74 (m, 2H), 3.51-3.54 (m, 2H), 3.12-3.14 (m, 2H), 2.85-2.95 (m, 4H, J=7.6 Hz), 2.55-2.65 (m, 3H), 2.08-2.12 (n, 4H), 2.03 (s, 12H), 1.96-2.02 (n, 4H). EIMS (m/z): 1037 (M$^-$+2Na).

EXAMPLE 11

Preparation of a Cyanine Dye-Photosensitizer Conjugate Having a Structure Shown in Formula XVII 0.11 mmol of an intermediate having a structure shown in formula XXI prepared in EXAMPLE 4 of the present invention, 0.074 mmol of a compound having a structure shown in formula XXVIII and 0.11 mmol of benzotriazol-1-yloxytri(dimethylamino)phosphonium hexafluorophosphate (BOP) were dissolved in anhydrous DMF to obtain a reaction solution. The above reaction solution was stirred at room temperature and in argon atmosphere for 12 hours. After completion of the reaction (monitored by TLC), the solvent was removed by suction filtration under reduced pressure, and the resulting crystals were washed with diethyl ether, to result in a product. The resulting product was further purified by preparative silica gel TLC with a mixed solution of dichloromethane and methanol (9:1 in volume ratio) as an eluent, resulting in a compound having a structure shown in formula XXIX, with a yield of 55%.

0.003 mmol of the above compound having the structure shown in formula XXIX and 0.33 mmol of 4-aminothiophenol were dissolved in anhydrous DMF, and stirred at room temperature and in nitrogen atmosphere for 12 hours. The resulting crystals were washed with diethyl ether, to result in a product. The resulting product was further purified by preparative silica gel TLC with a mixed solution of dichloromethane and methanol (86:17 in volume ratio) as an eluent, resulting in a compound having a structure shown in formula XVII, with a yield of 54%.

The cyanine dye-photosensitizer conjugate having the structure shown in formula XVII provided in the present invention was detected, with a result as follows:

UV-vis λmax (in MeOH): 660, 835 nm; 1HNMR (400 Mhz, CDCl3-10% CD3OD): δ 9.56 (singlet, 1H, meso-H), 9.55 (singlet, 1H, meso-H), 9.08 (brs, 2H, NH), 8.64 (d, 2H, J=14 Hz), 8.44 (singlet, 1H, meso-H), 8.39 (d, 2H, J=14 Hz), 7.89 (d, 2H, J=10.8 Hz), 7.80 (d, 2H, J=8.4 Hz), 7.70 (d, 2H, J=9.2 Hz), 7.61 (d, 2H, J=8.4 Hz), 7.41-7.44 (m, 4H), 7.24-7.36 (m, 4H), 6.84 (d, 2H, J=9.2 Hz), 6.41 (t, 2H, J=8 Hz), 6.01 (brs, 1H, NH), 5.75-5.79 (m, CH3CHOhexyl), 5.63 (brs, 1H, NH), 5.02 (dd, AB system 2H, 151-CH2, J=19.6 Hz), 4.58 (m, 1H, 17-H), 4.11 (m, 1H, H-18), 3.35-3.61 (m, 4H, 8-CH2CH3 & —OCH2-Hexyl), 3.05 (singlet, 3H, ring-CH3), 3.00 (singlet, 3H, ring-CH3), 2.27-2.73 (m, 21H, —(NHCH2)2-, ring-CH3, 172-CHH, 172-CHH, 171-CHH), 1.98 (d, 3H, CH3CH-Ohexyl, J=7.2 Hz), 1.15-1.88 (in, 20H), 1.21-1.49 (m, 17H, -2CH2-Hexyl), 171-CHH, 18-CH3, —CH2-Hexyl, —(NHCH2)2-), 8-CH2CH3, —CH2-Hexyl), 0.64 (t, 3H, CH3-Hexyl, J=6.8 Hz); EIMS (m/z): 1665 (M⁻+2Na).

EXAMPLE 12

Ultraviolet Spectroscopy Detection for Compounds Provided in the Present Invention Electronic absorption spectra for the compounds are shown in FIG. 1, from which it can be seen that, all the compounds having a structure shown in formula VIII, formula IX, formula III, formula IV, formula V, and formula XVII provided according to the present invention show a strong long-wavelength absorption peak between 750 nm and 860 nm, and have an obvious Stokes shift between 37 nm and 41 nm.

TABLE 1

Long-wavelength absorption peaks, fluorescences and Stokes shifts of synthesized compounds

| | Absorption peak (nm) | Fluorescence (nm) | Stokes shift (nm |
|---|---|---|---|
| Formula VIII | 831 | 872 | 41 |
| Formula IX | 837 | 876 | 39 |
| Formula III | 833 | 873 | 40 |
| Formula IV | 829 | 866 | 37 |
| Formula V | 825 | 864 | 39 |

EXAMPLE 13

Imaging Analysis of Compounds Provided in the Present Invention

BALB/c mice with CT26 colon tumor were selected, which were injected intravenously with a compound solution formulated from 1% Tween-80 and 5% glucose, at an i.v. dosage of 0.3 μmol/kg, so as to assess the capability of these compounds for in vivo absorption and fluorescent imaging in the mice. Whole-body imaging was performed on the mice at different time points, by using a long-pass filter, ex. 710~740 nm, em. 800 for imaging.

With an intermediate having a structure shown in formula XVIII as a control, the imaging effects of the compounds having structures shown in formula HI, IV and V were detected and analyzed. For each group of experiments, imaging test was performed on 3 mice individually, but for the imaging effect detection test of the compound having a structure shown in formula V, imaging was performed on 2 mice. The imaging effects for the mice were recorded 4, 8, 12, 24, 48, 72 and 96 hours after being injected into the compound solution, respectively.

Figure 4:
Figure 4:
Figure 4:
Figure 5:
Figure 5:

Among those, the whole-body imaging effect of the mice with injection of the intermediate having a structure shown in formula XVIII is shown in FIG. 2; the whole-body imaging effect of the mice with injection of the intermediate having a structure shown in formula III is shown in FIG. 3; the whole-body imaging effect of the mice with injection of the intermediate having a structure shown in formula IV is shown in FIG. 4; and the whole-body imaging effect of the mice with injection of the intermediate having a structure shown in formula V is shown in FIG. 5.

The detection results show that: the compound shown in formula III having a p-aminothioether group when imaging has a low background value and a better imaging effect; and the compounds connected with a structure of p-aminothioether group generally have a superior imaging effect to those without connection with a structure of 4-aminothioether group, and exhibit low background value

EXAMPLE 14

Detection of Absorption Ratio for Compounds Provided in the Present Invention

BALB/c mice with CT26 colon tumor were selected, which were injected intravenously with a compound solution formulated from 1% Tween-80 and 5% glucose, at an i.v. dosage of 0.3 μmol/kg, so as to assess the capability of these compounds for in vivo absorption and fluorescent imaging in the mice. Whole-body imaging was performed on the mice at different time points, by using a long-pass filter, ex. 710~740 nm, em. 800 for imaging.

Figure 6:
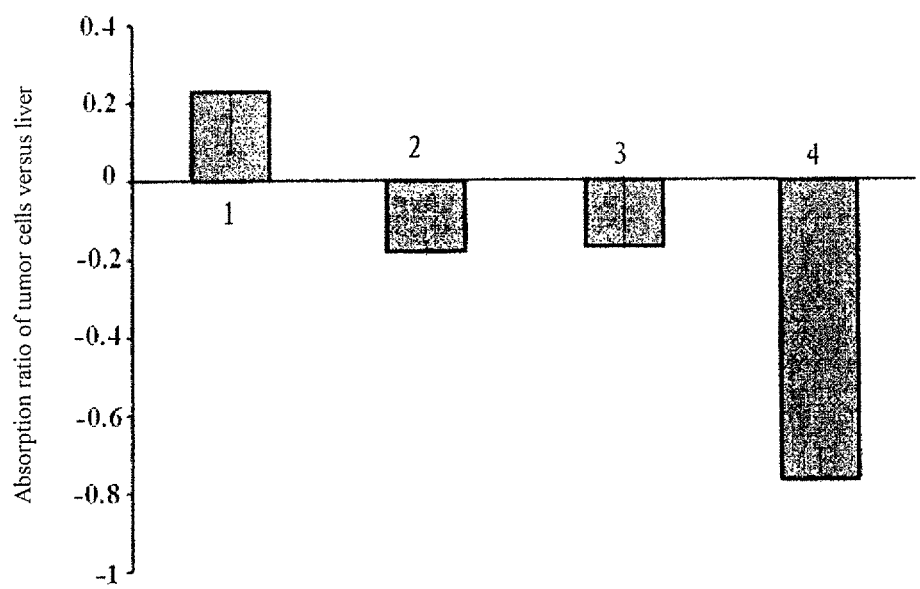
FIG. 6 shows absorption ratio of the tumor cells versus liver to the compound provided according to the present invention 24 hours after injection, in which column 1 shows the absorption ratio to the compound having a structure shown in formula III provided in the present invention for the tumor cells verse liver; column 2 shows the absorption ratio to the compound having a structure shown in formula IV provided in the present invention for the tumor cells verse liver; column 3 shows the absorption ratio to the compound having a structure shown in formula V provided in the present invention for the tumor cells verse liver; and column 4 shows the absorption ratio to the compound having a structure shown in formula VIII provided in the present invention for the tumor cells verse liver.

Imaging effects of the compounds having structures shown in formula VIII, formula III, formula IV and formula V were detected and analyzed. For each group of experiments, imaging test was performed on 3 mice individually, and imaging effects of the mice 24 hours after being injected into the compound solution were recorded, and calculated the ratio between absorption of the tumor to the compounds and absorption of the liver to the compounds, with the results shown in FIG. 6. From this figure, it can be seen that, in all the cyanine dye compounds, compounds containing a p-aminothioether group, such as the compound having a structure as shown in formula III show the best absorption activity. Moreover, the compounds with connection to a p-aminothioether group generally have a higher absorption activity than the compounds without connection to a p-aminothioether group.

EXAMPLE 15

Figure 7:
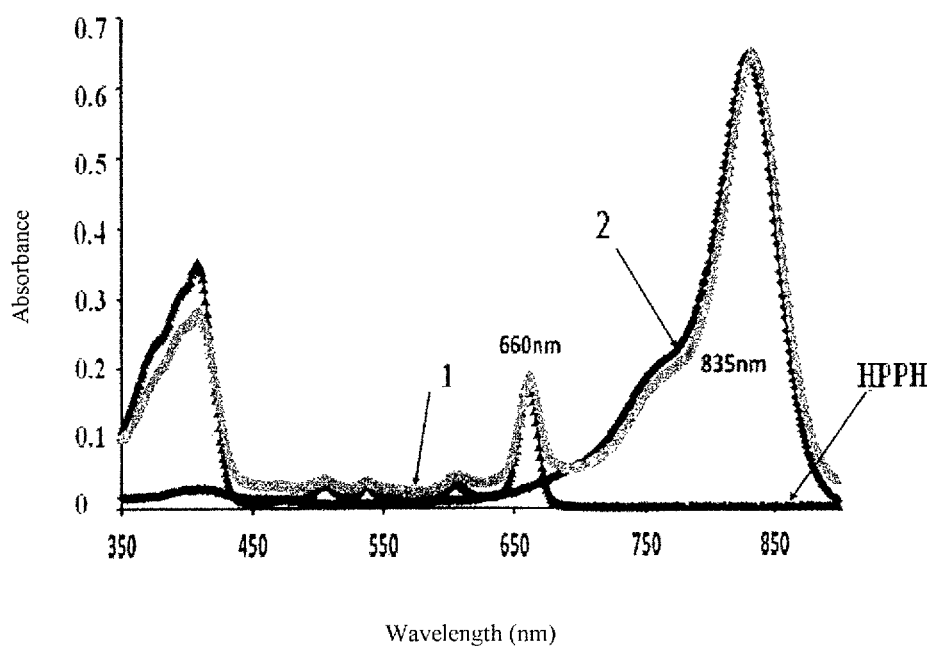
FIG. 7 shows electronic absorption spectra for the compounds provided according to the present invention, in which, with HPPH as a control, curve 1 shows electronic absorption spectrum for the compound having a structure shown in formula XVII; and curve 2 shows electronic absorption spectrum for the compound having a structure shown in formula III.

Electronic Absorption Spectra for Dual-Function Agents for Tumor Imaging and Tumor Treatment Provided in the Present Invention Electronic absorption spectroscopy of the dual-function agents for tumor imaging and tumor treatment provided in the present invention (compounds having a structure shown in formula III and formula XVII) were detected in methanol at an equimolar concentration (5 μmol/L), as shown in FIG. 7. Meanwhile, a commercially available cyanine dye compound HPPH was selected as a control. From the figure, it can be seen that, the compounds having structures shown in formula III and formula XVII have an obvious absorption peak at 660 nm and 835 nm, respectively, which is in line with the expected value.

EXAMPLE 16

Analysis of In Vivo Fluorescent Imaging Effects for a Dual-Function Agent for Tumor Imaging and Tumor Treatment Provided in the Present Invention 3 BALB/c mice with CT26 colon tumor were injected with a compound having a structure shown in formula XVII at an injection dosage of 0.3 μmol/kg, respectively. The best imaging effect was obtained 24 hours after injection, with the results thereof shown in FIG. 8. The data show that, the compound having a structure shown in formula XVII has good capability for tumor imaging and a low background value, which can clearly identify the location of a tumor tissue.

EXAMPLE 17

Detection of Absorption Efficiency of a Dual-Function Agent for Tumor Imaging and Tumor Treatment Provided in the Present Invention In order to reflect pulmonary metastatic tumor, 100000 CT26 colon tumor cells were injected intravenously into a BALB/c mouse for growth for about 2 weeks. A mouse without intravenous injection of CT26 colon tumor cells and the mouse which had been injection into CT26 colon tumor cells were injected with a compound having a structure shown in formula III at a dosage of 0.3 μmol/kg. The in vivo imaging of the two mice 24 hours after injection is shown in FIG. 9. It can be seen from this figure that, the compound has been accumulated in the liver of both the mice, but the dye in the lung of the mouse with tumor cells is significantly more than the compound in the lung of the mouse free of tumor cells (as shown at a depth of 7 mm~15 mm).

A compound and preparation method thereof, as well as an intermediate for synthesis of the compound and application of the compound in photodynamic therapy have been demonstrated in detail above. Specific examples are given herein to illustrate the principle and embodiments of the present invention, and the illustration of these examples is only intended to facilitate understanding of the methods of the present invention and core concept thereof. It should be noted that, several improvements and modifications may be made by those skilled in the art to the present invention without departing from the principle of the present invention, which improvements and modifications also fall within the protection scope of the claims thereof.

The invention claimed is:
1. A compound having a structure as shown in formula I,

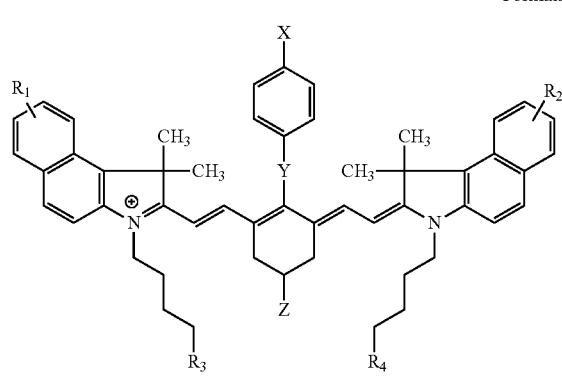

Formula I wherein $R_1$ and $R_2$ are independently selected from hydrogen, alkaryl, fluorinated groups, and sulfonated groups;
$R_3$ and $R_4$ are independently selected from —H, —SO$_3$H, —SO$_3$Na, —COOH, —OH, and —NH$_2$;
X is NH$_2$;
Y is selected from —O— and —S—; alternatively, Y is absent, being a single bond;
Z is selected from —COOH, —COOEt, and —CO—NH-A$_4$;
A$_4$ is —C$_6$H$_5$, —(CH$_2$)$_n$-PS, in which n=0 to 6; and PS is glycosyl, tetrapyrrole ring or reduced tetrapyrrole ring, RGD peptide, iRGD peptide, DOTA or DTPA;
the tetrapyrrole ring includes, but is not limited to, chlorin, bacteriochlorin, purpurin imide and rhodopurpurin imide.

2. The compound according to claim 1, wherein the compound has a structure as shown in formula II,

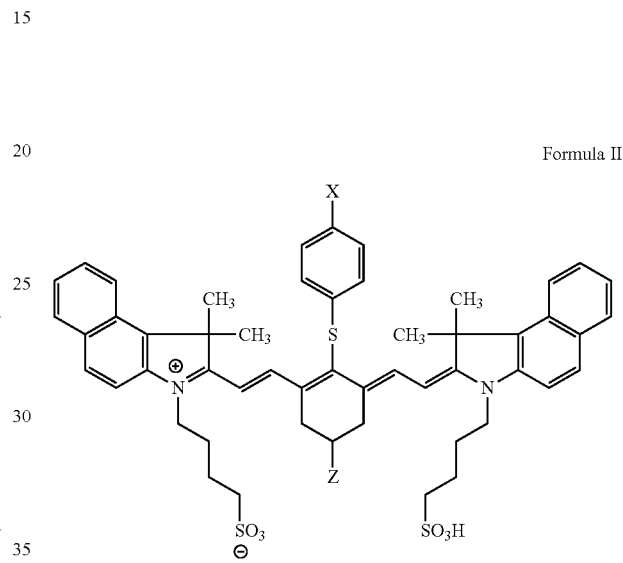

Formula II wherein X is —NH$_2$;
Z is any one of —COOH, —COOEt, and —CO—NH-A$_4$;
A$_4$ is —C$_6$H$_5$, DOTA, or DTPA.

3. The compound according to claim 2, wherein the compound has a structure as shown in any one of formula IV to formula VII, and Formula X,

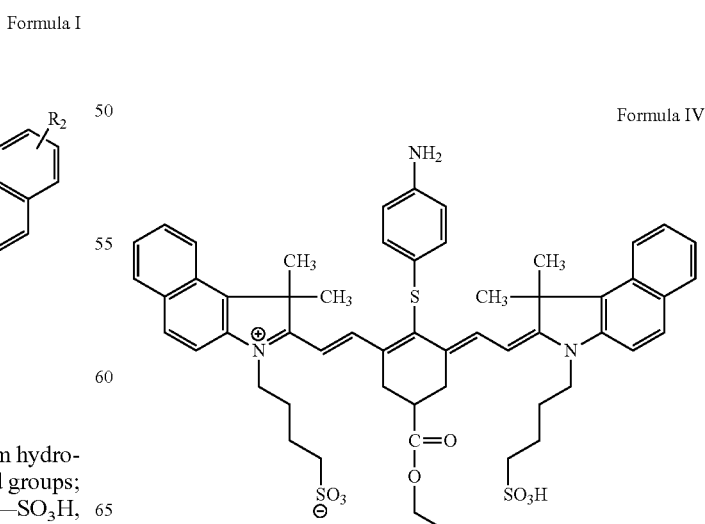

Formula IV

Formula V

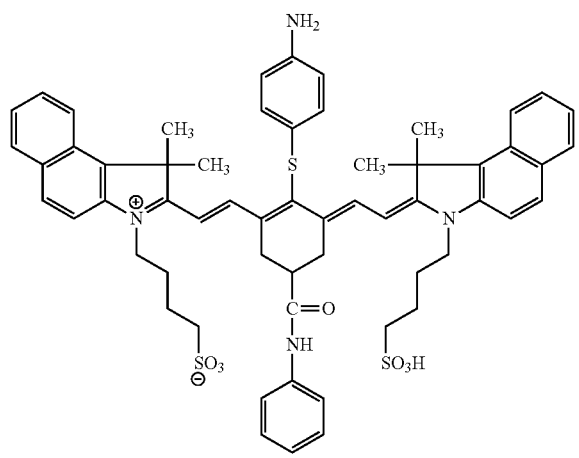

Formula VI

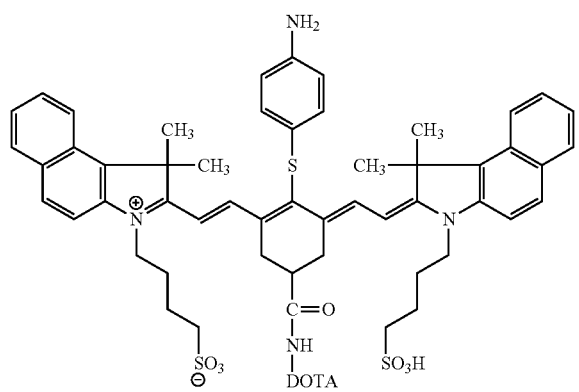

Formula VII

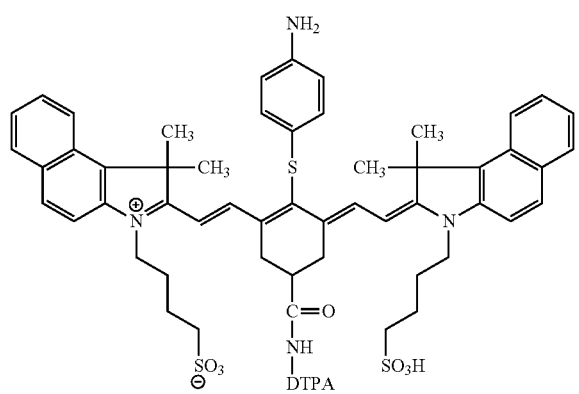

Formula X

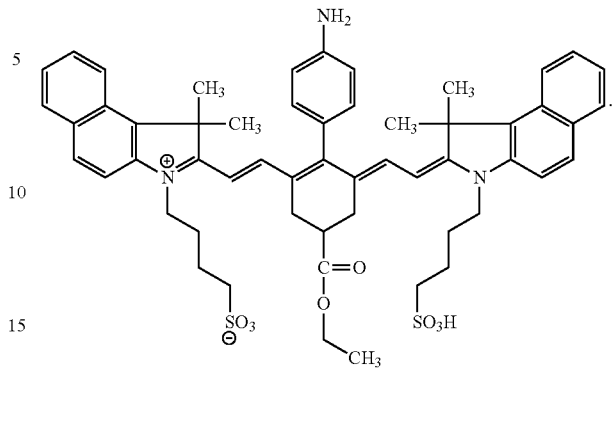

4. The compound according to claim 1, wherein the compound has a structure as shown in formula XI, Formula XI

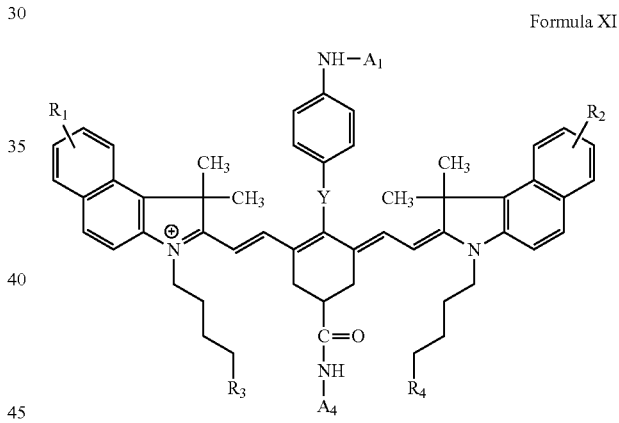

wherein Y is O or S; alternatively, Y is absent, being a single bond;

$R_1$ and $R_2$ are independently selected from hydrogen, alkaryl, fluorinated groups or sulfonated groups;

$R_3$ and $R_4$ are independently selected from —H, —SO$_3$H, —SO$_3$Na, —COOH, —OH or —NH$_2$;

$A_1$ is —H;

$A_4$ is —(CH$_2$)$_n$-PS, in which n=0 to 6; and PS is glycosyl, tetrapyrrole ring or reduced tetrapyrrole ring, RGD peptide, iRGD peptide, DOTA, or DTPA;

the tetrapyrrole ring includes, but is not limited to, chlorin, bacteriochlorin, purpurin imide and rhodopurpurin imide.

5. The compound according to claim 4, wherein the compound has a structure as shown in formula XII, Formula XII

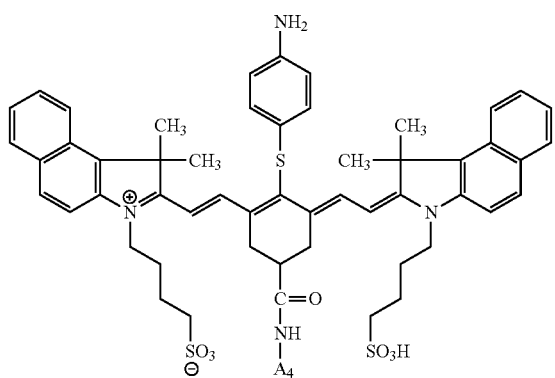

wherein $A_4$ is RGD peptide, iRGD peptide, glycosyl, DTPA, DOTA, triamino ester or —$(CH_2)_n$-PS, in which n=0 to 6, and PS has a structure as shown in formula XIII, formula XIV or formula XV;

Formula XIII

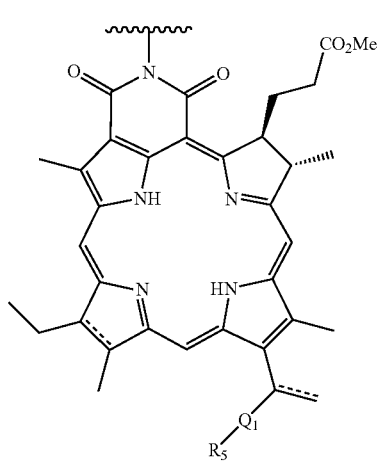

Formula XIV

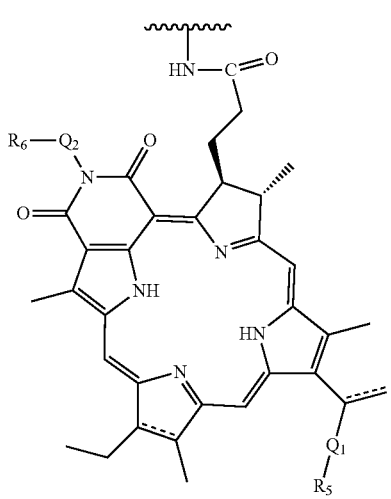

Formula XV

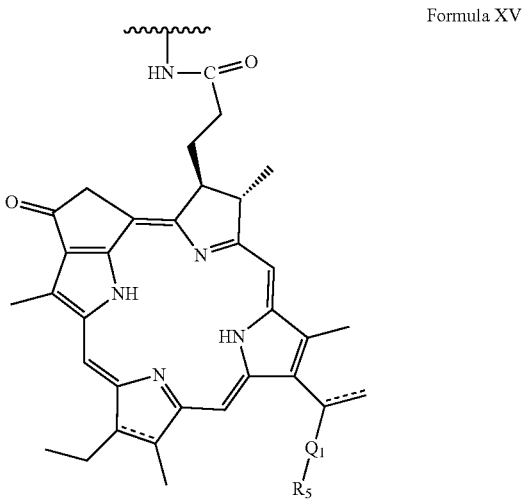

wherein === represents a single bond or a double bond; $Q_1$ and $Q_2$ are independently —O—, alkyl, aryl or reduced aryl; $R_5$ and $R_6$ are independently alkyl or alkyl labelled with F-18, iodobenzyl, or iodobenzyl labelled with I-124.

6. The compound according to claim 4, wherein the compound has a structure as shown in formula XVI or formula XVII, Formula XVI

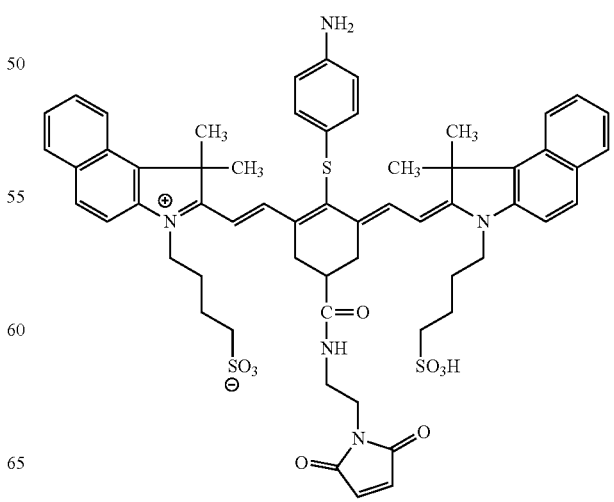

Formula XVII

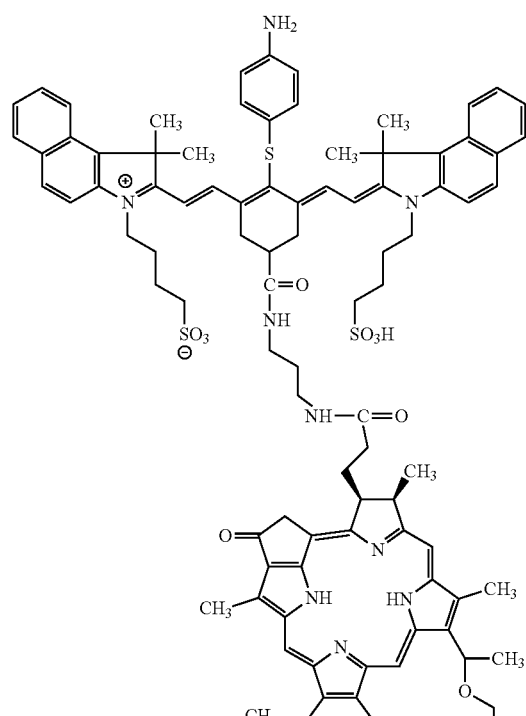

Formula III

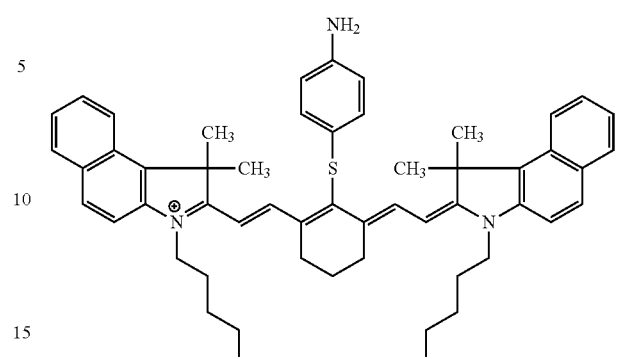

Formula IV

Formula V

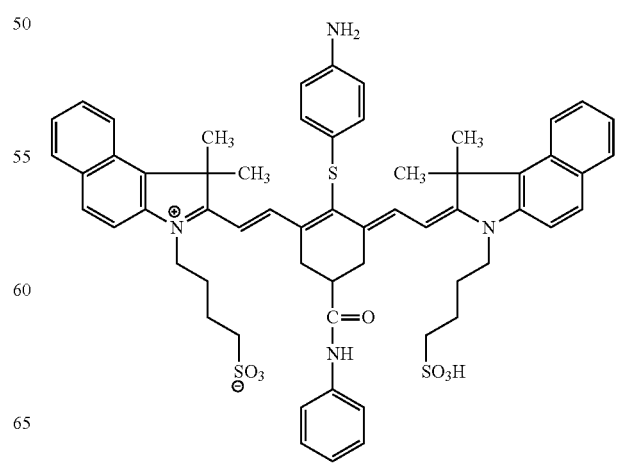

7. A preparation method for the compound of claim 3 having a structure as shown in formula III, formula IV, formula V, formula VIII or formula IX, wherein the method comprises steps of:

step 1: subjecting a compound having a structure as shown in formula XXIII to a first Vilsmeier-Haack-Arnold reaction in the presence of phosphoryl chloride, DMF and aniline, to produce a compound having a structure as shown in formula XXIV;

step 2: subjecting the compound having the structure as shown in formula XXIV to a first substitution reaction with a compound having a structure shown in formula XXV, to produce an intermediate having a structure shown in formula XVIII, formula XIX or formula XX; and step 3: subjecting the intermediate having the structure shown in formula XVIII, formula XIX or formula XX to a fourth substitution reaction with a compound having a structure shown in formula XXVII, respectively, to obtain the compound having the structure as shown in formula III, formula IV, formula V, formula VIII or formula IX;

Formula VIII
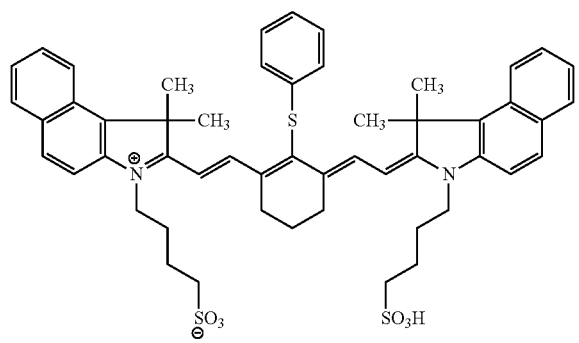
Formula XX
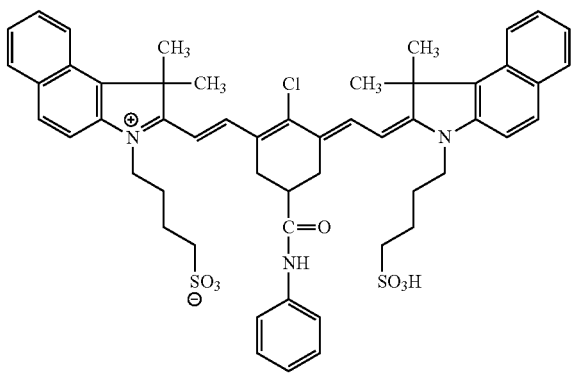
Formula IX
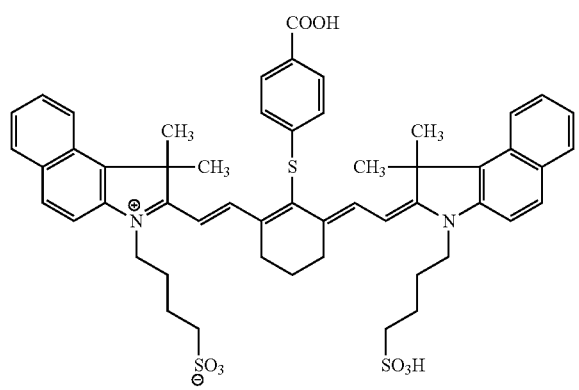
Formula XXIII
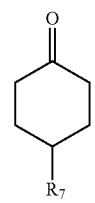
Formula XXIV
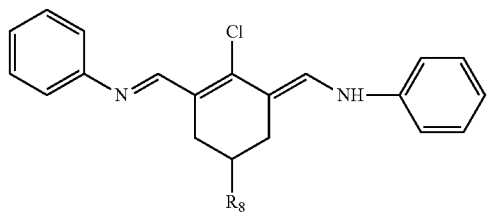
Formula XVIII
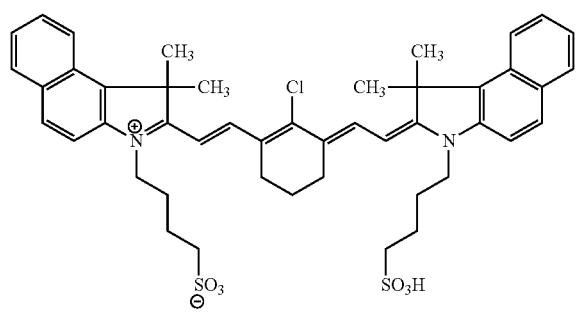
Formula XXV
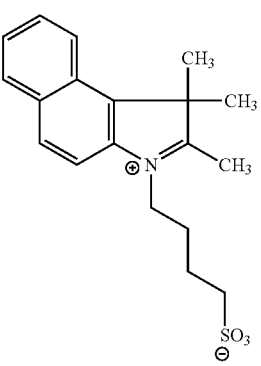
Formula XIX
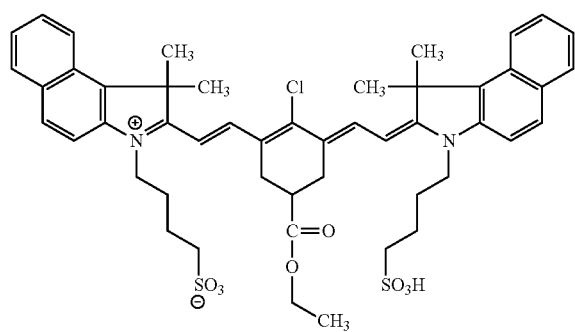
Formula XXVII
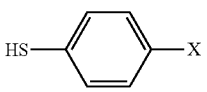
wherein $R_7$ is selected from —H,
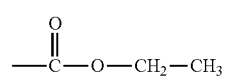

or —COOH; $R_8$ is selected from —H,

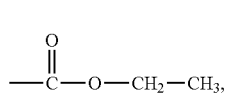 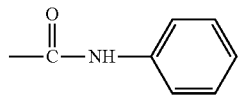

or —COOH; and X is selected from —H, —COOH or —NH$_2$.

8. A preparation method for the compound of claim 3 having a structure as shown in formula X, wherein the method comprises steps of:

step 1: subjecting a compound having a structure as shown in formula XXIII to a third Vilsmeier-Haack-Arnold reaction in the presence of phosphoryl chloride, DMF and aniline, to produce a compound having a structure as shown in formula XXIV;

step 2: subjecting the compound having the structure as shown in formula XXIV to a fifth substitution reaction with a compound having a structure shown in formula XXV, to produce an intermediate having a structure shown in formula XIX; and step 3: subjecting the intermediate having the structure shown in formula XIX to a sixth substitution reaction with 4-aminophenylboronic acid under the catalysis of Pd(PPh$_3$)$_4$, to obtain the compound having the structure as shown in formula X;

Formula X

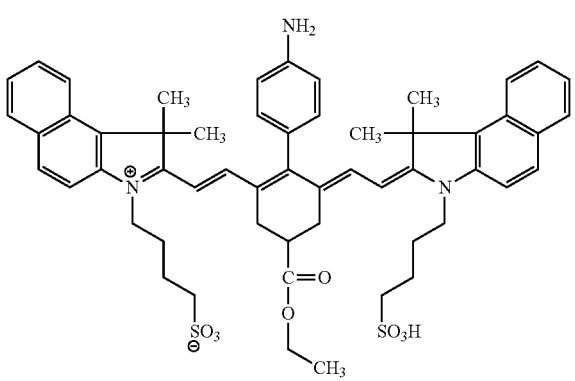

Formula XIX

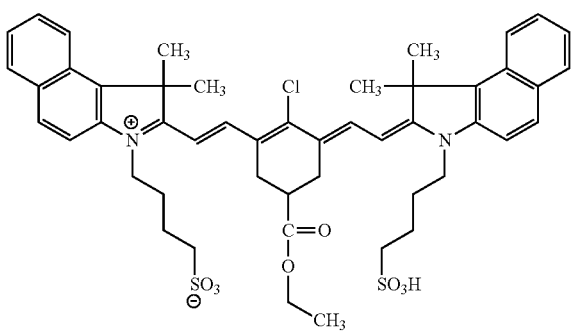

Formula XXIII

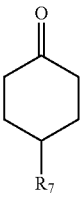

Formula XXIV

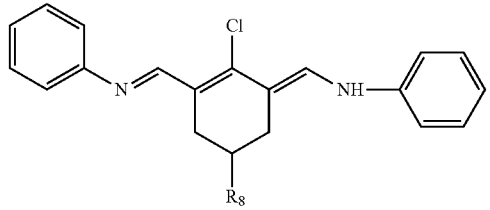

Formula XXV

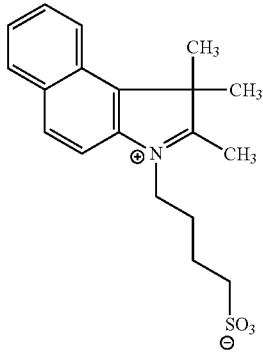

wherein $R_7$ is —COOH; and $R_8$ is

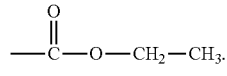

9. A preparation method for a compound having a structure as shown in formula VI, formula VII or formula XVII, wherein the method comprises steps of:

step 1: subjecting 4-carboxyl cyclohexanone to a second Vilsmeier-Haack-Arnold reaction in the presence of phosphoryl chloride and DMF, to produce a compound having a structure as shown in formula XXVI;

step 2: subjecting the compound having the structure as shown in formula XXVI to a second substitution reaction with a compound having a structure shown in formula XXV, to produce an intermediate having a structure shown in formula XXI;

step 3: subjecting the intermediate having the structure shown in formula XXI to a third substitution reaction with a compound having a structure shown in formula XXVII, DOTA-NH$_2$ or DTPA-NH$_2$ in the presence of BOP and DMF, to produce an intermediate having a structure shown in formula XXIX, formula XXX or formula XXXI; and step 4: subjecting the intermediate having the structure as shown in formula XXIX, formula XXX or formula XXXI to a seventh substitution reaction with 4-aminothiophenol, to obtain the compound having the structure as shown in formula VI, formula VII or formula XVII;

Formula XXVI
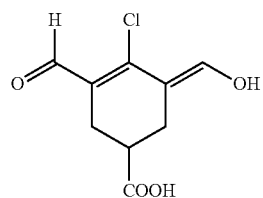
Formula XXV
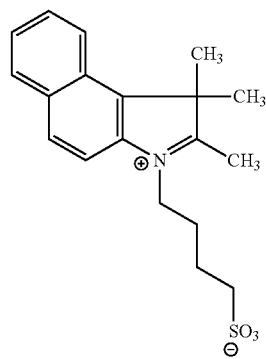
Formula XXI
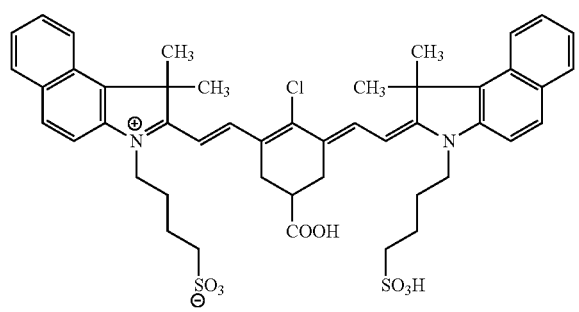
Formula XXIX
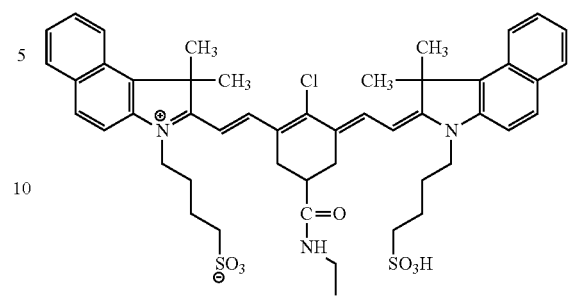
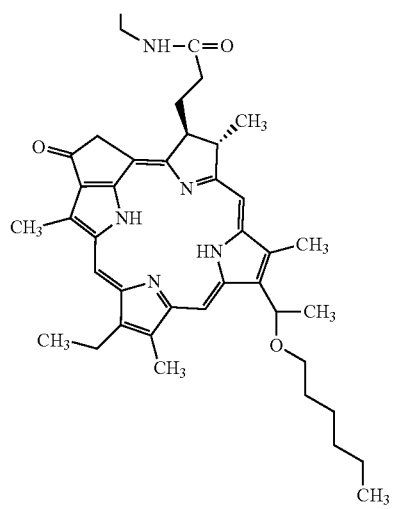
Formula XXVIII
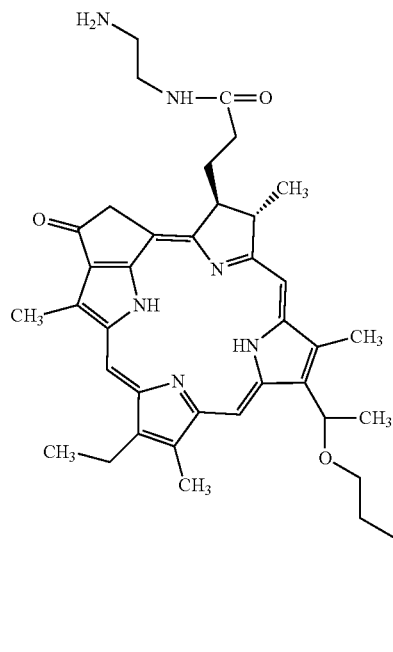
Formula XXX
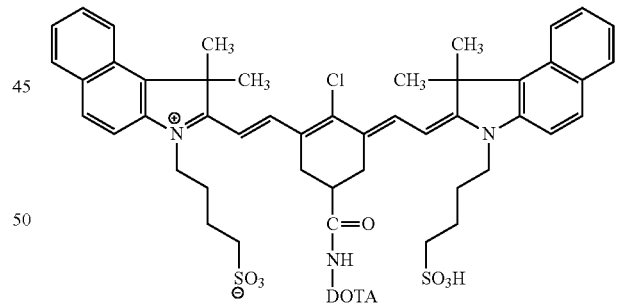
Formula XXXI
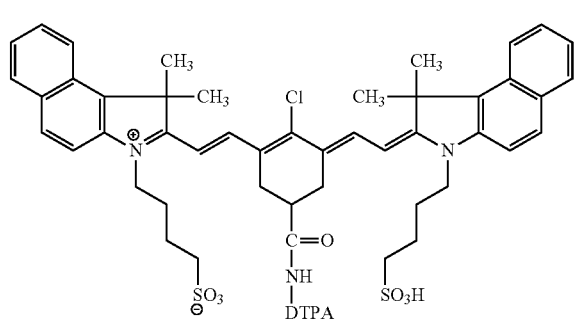

Formula VI
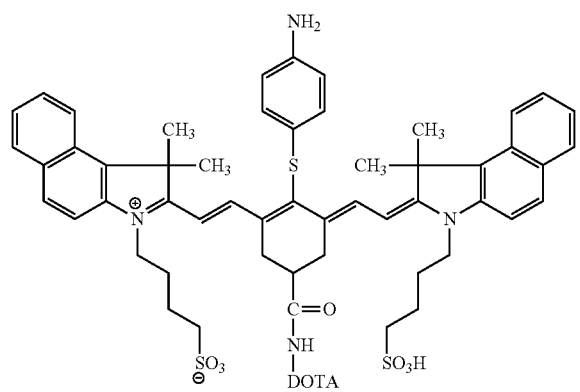
Formula VII
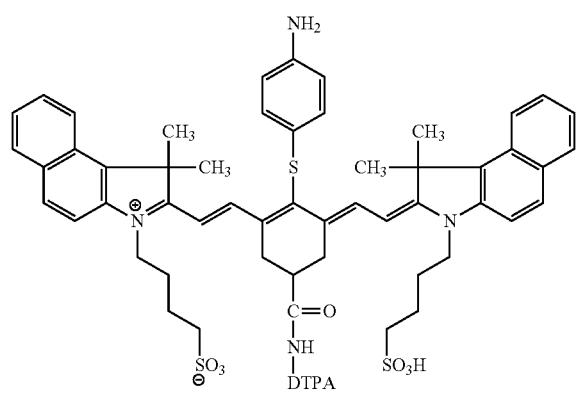
Formula XVII
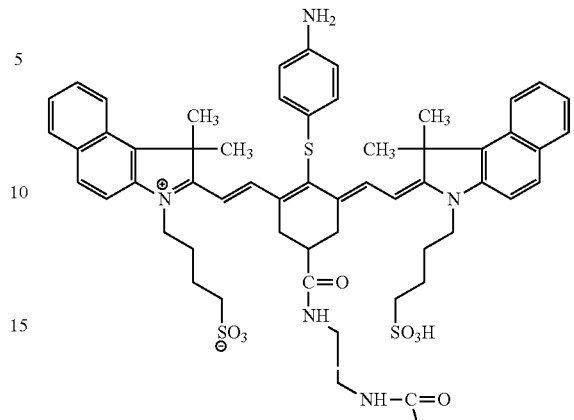
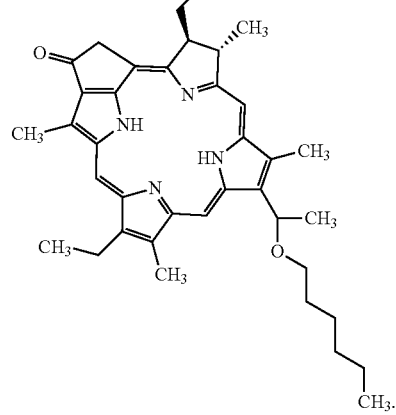
* * * * *